United States Patent [19]
Gaster et al.

[11] Patent Number: 5,852,014
[45] Date of Patent: Dec. 22, 1998

[54] CONDENSED INDOLE DERIVATIVES AS 5HT$_4$-RECEPTOR ANTAGONISTS

[75] Inventors: Laramie Mary Gaster, Bishop's Stortford; Paul Adrian Wyman, Epping, both of England

[73] Assignee: SmithKline Beecham p.l.c., Brentford, England

[21] Appl. No.: 459,168

[22] Filed: Jun. 2, 1995

Related U.S. Application Data

[63] Continuation-in-part of Ser. No. 302,784, filed as PCT/GB93/00506, Mar. 10, 1993, abandoned.

[30] Foreign Application Priority Data

| Mar. 12, 1992 | [GB] | United Kingdom | 9205428 |
| Sep. 5, 1992 | [GB] | United Kingdom | 9218846 |
| Dec. 29, 1992 | [GB] | United Kingdom | 9227045 |

[51] Int. Cl.$^6$ .................. H61K 31/535; C07D 498/04
[52] U.S. Cl. .................. 514/230.2; 514/211; 514/214; 514/220; 514/224.6; 514/248; 514/294; 514/321; 514/322; 514/323; 514/366; 514/375; 514/393; 540/547; 540/561; 540/586; 544/32; 544/89; 544/252; 546/94; 546/198; 546/199; 546/200; 546/150; 546/217; 546/302.4; 546/428
[58] Field of Search .................. 544/89; 514/230.2

[56] References Cited

U.S. PATENT DOCUMENTS

| 4,314,058 | 2/1982 | Hayami et al. | 542/455 |
| 5,001,133 | 3/1991 | Richardson et al. | 514/304 |
| 5,705,498 | 1/1998 | Gaster et al. | 514/214 |

FOREIGN PATENT DOCUMENTS

| 36269 | 3/1981 | European Pat. Off. |
| 0144986 | 6/1985 | European Pat. Off. |
| 328 200 | 2/1989 | European Pat. Off. |
| 429 984 A3 | 11/1990 | European Pat. Off. |
| 0 485 962 | 11/1991 | European Pat. Off. |
| 501 322 | 2/1992 | European Pat. Off. |
| 1593146 | 1/1978 | United Kingdom. |
| 2125398 | 6/1983 | United Kingdom. |
| 1 566 307 | 12/1995 | United Kingdom. |
| WO91/16045 | 10/1991 | WIPO. |
| WO93/02677 | 2/1993 | WIPO. |
| WO93/03725 | 3/1993 | WIPO. |
| WO93/05038 | 3/1993 | WIPO. |
| WO93/05040 | 3/1993 | WIPO. |
| WO93/08187 | 4/1993 | WIPO. |
| WO93/12785 | 7/1993 | WIPO. |
| WO93/14745 | 8/1993 | WIPO. |
| WO93/16072 | 8/1993 | WIPO. |
| 9318036 | 9/1993 | WIPO. |
| WO93/18027 | 9/1993 | WIPO. |
| WO93/24117 | 12/1993 | WIPO. |
| WO94/00113 | 1/1994 | WIPO. |
| WO94/01095 | 1/1994 | WIPO. |
| WO94/05654 | 3/1994 | WIPO. |
| WO94/07859 | 4/1994 | WIPO. |
| WO94/08965 | 4/1994 | WIPO. |
| WO94/08994 | 4/1994 | WIPO. |
| WO94/08995 | 4/1994 | WIPO. |
| WO94/08998 | 4/1994 | WIPO. |
| WO94/10174 | 5/1994 | WIPO. |
| WO94/17071 | 8/1994 | WIPO. |
| WO94/19344 | 9/1994 | WIPO. |
| WO94/27987 | 12/1994 | WIPO. |
| WO94/29298 | 12/1994 | WIPO. |
| WO95/04737 | 2/1995 | WIPO. |

OTHER PUBLICATIONS

Dumuis, et al., "The gastrointestinal prokinetic benzamide derivatives are agonists at the non-classical 5-HT receptor (5-HT4) positively coupled to adenylate cyclase neurons", *Archives of Pharmacology*, 340:pp. 403–410 (1989).

Dumius, et al., "A-5HT receptor in central nervous system positively coupled with adenylate cyclase, is antagonized by ICS 205 930", *European Journal of Pharmacology*, 146:pp. 187–188 (1988).

A. J. Kaumann, "Piglet sinoatrial 5–HT receptors resemble human atrial 5–HT$_4$–like receptors", *Archives of Pharmacology*, 342, pp. 619–622 (1990).

Dumius et al., "A Nonclassical 5–Hydroxytruptamine Receptor Positively Coupled with Adenylate Cyclase in the Central Nervous System", *Mol. Pharmacology*, 34, pp. 880–887 (1988).

Welch et al., "Biochemical Comparison of Migraine and Stroke", *Headache*, 16, pp. 160–167 (1976).

Saxena, P.R. *Pharmacology and Therapeutics*, vol. 66, pp. 339–368 (1995).

Dhasmana, K.M., et al *Life Sciences*, vol. 53, pp. 1651–1661 (1993).

*Primary Examiner*—Richard L. Raymond
*Attorney, Agent, or Firm*—Soma G. Simon; Charles M. Kinzig; Edward T. Lentz

[57] ABSTRACT

Compounds of formula (I) and pharmaceutically acceptable salts thereof:

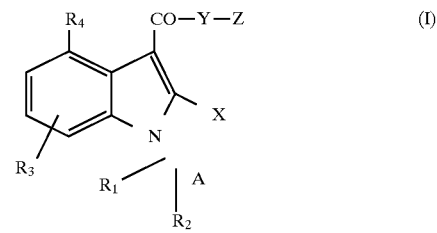

and their use as pharmaceuticals in the treatment of gastrointestinal disorders, cardiovascular disorders and CNS disorders.

6 Claims, No Drawings

CONDENSED INDOLE DERIVATIVES AS 5HT$_4$-RECEPTOR ANTAGONISTS

This is a continuation-in-part application of U.S. Ser. No. 08/302,784, filed as PCT/GB93/00506, Mar. 10, 1993, now abandoned.

This invention relates to novel compounds having pharmacological activity, to a process for their preparation and to their use as pharmaceuticals.

EP-A-429984 (Nisshin Flour Milling Co., Ltd.) describes indole derivatives having 5-HT$_3$ receptor antagonist activity.

European Journal of Pharmacology 146 (1988), 187–188, and Naunyn-Schmiedeberg's Arch. Pharmacol. (1989) 340:403–410, describe a non classical 5-hydroxytryptamine receptor, now designated the 5-HT$_4$ receptor, and that ICS 205–930, which is also a 5-HT$_3$ receptor antagonist, acts as an antagonist at this receptor.

WO 91/16045 (SmithKline and French Laboratories Limited) describes the use of cardiac 5-HT$_4$ receptor antagonists in the treatment of atrial arrhythmias and stroke.

EP-A-501322 (Glaxo Group Limited) describes indole derivatives having 5-HT$_4$ antagonist activity.

A class of novel, structurally distinct compounds has now been discovered, which compounds are indole derivatives 1,2-disubstituted by alkyleneoxy, with an azacyclic, fused azabicyclic or aminoalkyl moiety. These compounds have 5-HT$_4$ receptor antagonist activity.

Accordingly, the present invention provides a compound of formula (I), or a pharmaceutically acceptable salt thereof:

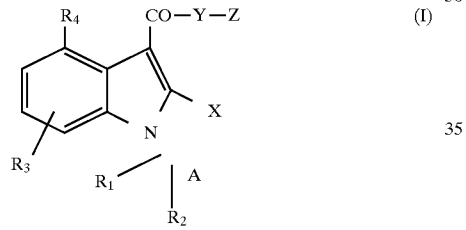

wherein
X is O, S, SO, SO$_2$, CH$_2$, CH or NR wherein R is hydrogen or C$_{1-6}$ alkyl;
A is a saturated or unsaturated polymethylene chain of 2–4 carbon atoms;
R$_1$ and R$_2$ are hydrogen or C$_{1-6}$ alkyl;
R$_3$ is hydrogen, halo, C$_{1-6}$ alkyl, amino, nitro or C$_{1-6}$ alkoxy;
R$_4$ is hydrogen, halo, C$_{1-6}$ alkyl or C$_{1-6}$ alkoxy;
Y is O or NH;
Z is of sub-formula (a), (b) or (c):

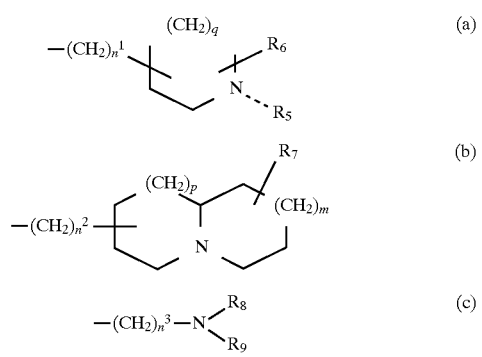

wherein
n$^1$ is 1, 2, 3 or 4; n$^2$ is 0, 1, 2, 3 or 4; n$^3$ is 2, 3, 4 or 5;
q is 0, 1, 2 or 3; p is 0, 1 or 2; m is 0, 1 or 2;
R$_5$ is hydrogen, C$_{1-12}$ alkyl, aralkyl or R$_5$ is (CH$_2$)$_z$—R$_{10}$ wherein z is 2 or 3 and R$_{10}$ is selected from cyano, hydroxyl, C$_{1-6}$ alkoxy, phenoxy, C(O)C$_{1-6}$ alkyl, COC$_6$H$_5$, —CONR$_{11}$R$_{12}$, NR$_{11}$COR$_{12}$, SO$_2$NR$_{11}$R$_{12}$ or NR$_{11}$SO$_2$R$_{12}$ wherein R$_{11}$ and R$_{12}$ are hydrogen or C$_{1-6}$ alkyl; and
R$_6$, R$_7$ and R$_8$ are independently hydrogen or C$_{1-6}$ alkyl; and
R$_9$ is hydrogen or C$_{1-10}$ alkyl;
or a compound of formula (I) wherein the CO—Y linkage is replaced by a heterocyclic bioisostere;
having 5-HT$_4$ receptor antagonist activity.

Examples of alkyl or alkyl containing groups include C$_1$, C$_2$, C$_3$, C$_4$, C$_5$, C$_6$, C$_7$, C$_8$, C$_9$, C$_{10}$, C$_{11}$ or C$_{12}$ branched, straight chained or cyclic alkyl, as appropriate. C$_{1-4}$ alkyl groups include methyl, ethyl, n- and iso-propyl, n-, iso-, sec- and tert-butyl. Cyclic alkyl includes cyclopropyl, cyclobutyl, cyclopentyl, cyclohexyl, cycloheptyl and cyclooctyl.

Aryl includes phenyl and naphthyl optionally substituted by one or more substituents selected from halo, C$_{1-6}$ alkyl and C$_{1-6}$ alkoxy.

Halo includes fluoro, chloro, bromo and iodo.

A suitable bioisostere for the amide or ester linkage containing Y in formula (I), is of formula (d):

wherein
the dotted circle represents one or two double bonds in any position in the 5-membered ring; H, J and I independently represent oxygen, sulphur, nitrogen or carbon, provided that at least one of H, J and I is other than carbon; U represents nitrogen or carbon.

Suitable examples of (d) are as described for X, Y and Z in EP-A-328200 (Merck Sharp & Dohme Ltd.), such as an oxadiazole moiety.

X is often O.

Values for A include —CH$_2$—(CH$_2$)$_r$—CH$_2$— wherein r is 0, 1 or 2; —CH$_2$—CH=CH—; —C(CH$_3$)=CH— or when X is CH or N, A may be —(CH$_2$)$_2$—CH= or —CH=CH—CH=. Other examples of A are as described in the examples hereinafter.

R$_1$ and R$_2$ are often hydrogen or R$_1$ and R$_2$ are gem-dimethyl.

r is often 1.

R$_3$ is preferably hydrogen.

R$_4$ is preferably hydrogen or halo, such as fluoro.

Y is preferably O or NH.

When Z is of sub-formula (a), n$^1$ is preferably 2, 3 or 4 when the azacycle is attached at the nitrogen atom and n$^1$ is preferably 1 when the azacycle is attached at a carbon atom, such as the 4-position when q is 2.

When Z is of sub-formula (b), n$^2$ is preferably such that the number of carbon atoms between the ester or amide linkage is from 2 to 4 carbon atoms.

Suitable values for p and m include p=m=1; p=0, m=1, p=1, m=2, p=2,m=1.

When Z is of sub-formula (c), n$^3$ is preferably 2, 3 or 4.

R$_8$ and R$_9$ are preferably both alkyl, especially one of R$_8$ and R$_9$ is C$_4$ or larger alkyl.

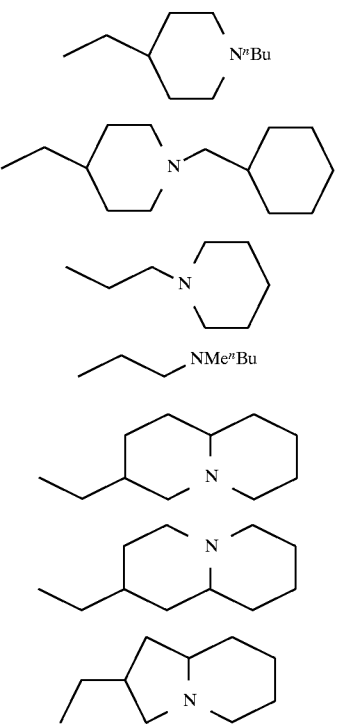

The invention also provides novel compounds within formula (I) with side chains (i), (ii), (iii), (iv), (v), (vi) or (vii). In a further aspect, the piperidine ring in (i), (ii) or (iii) may be replaced by pyrrolidinyl or azetidinyl, and/or the N-substituent in (i) or (ii) may be replaced by $C_3$ or larger alkyl or optionally substituted benzyl.

The present invention provides a compound of formula (I) wherein $R_5$ is 3-phenoxypropyl, in particular a compound of formula analogous to. E3 described hereafter wherein the n-butyl $R_5$ substituent is replaced by phenoxypropyl.

In an alternative aspect, the N-substituent in formula (i) or (ii) may be replaced by $(CH_2)_n R^4$ as defined in formula (I) of EP-A-501322 and in relation to the specific examples of EP-A-501322.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

Examples of pharmaceutically acceptable salts include quaternary derivatives of the compounds of formula (I) such as the compounds quaternised by compounds $R_X$-T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of T include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

It will also be realised that the $(CH_2)_n 2$ moiety in compounds of formula (I) wherein Z is (b), may adopt an α or β or configuration with respect to the fused azabicyclic moiety.

The compounds of formula (I) may be prepared by conventional coupling of the indole moiety with Z. Suitable methods are as described in GB 2125398A (Sandoz Limited), GB 1593146A and EP-A-36269 (Beecham Group p.l.c.), EP-A-429984 (Nisshin Flour Milling Co.) and EP-A-328200 (Merck Sharp & Dohme Limited). Reference is also made to EP-A-501322 (Glaxo Group Limited). It will be appreciated that the $(CH_2)_r$—O containing ring or $R_3/R_4$ introduction/modification may be carried out before or after coupling.

Aza(bi)cyclic side chain intermediates are known compounds or may be prepared according to the methods described in WO 93/03725 and WO 93/05040 (SmithKline Beecham p.l.c.).

The compounds of the present invention are 5-$HT_4$ receptor antagonists and it is thus believed may generally be used in the treatment or prophylaxis of gastrointestinal disorders, cardiovascular disorders and CNS disorders.

They are of potential interest in the treatment of irritable bowel syndrome (IBS), in particular the diarrhoea aspects of IBS, i.e., these compounds block the ability of 5-HT to stimulate gut motility via activation of enteric neurones. In animal models of IBS, this can be conveniently measured as a reduction of the rate of defaecation. They are also of potential use in the treatment of urinary incontinence which is often associated with IBS.

They may also be of potential use in other gastrointestinal disorders, such as those associated with upper gut motility, and as antiemetics. In particular, they are of potential use in the treatment of the nausea and gastric symptoms of gastro-oesophageal reflux disease and dyspepsia. Antiemetic activity is determined in known animal models of cytotoxic-agent/radiation induced emesis.

Specific cardiac 5-$HT_4$ receptor antagonists which prevent atrial fibrillation and other atrial arrhythmias associated with 5-HT, would also be expected to reduce occurrence of stroke (see A. J. Kaumann 1990, Naumyn-Schmiedeberg's Arch. Pharmacol. 342, 619–622, for appropriate animal test method).

Anxiolytic activity is likely to be effected via the hippocampus (Dumuis et al 1988, Mol Pharmacol., 34, 880–887). Activity can be demonstrated in standard animal models, the social interaction test and the X-maze test.

Migraine sufferers often undergo situations of anxiety and emotional stress that precede the appearance of headache (Sachs, 1985, Migraine, Pan Books, London). It has also been observed that during and within 48 hours of a migraine attack, cyclic AMP levels are considerably increased in the cerebrospinal fluid (Welch et al., 1976, Headache 16, 160–167). It is believed that a migraine, including the prodomal phase and the associated increased levels of cyclic AMP are related to stimulation of 5-$HT_4$ receptors, and hence that administration of a 5-$HT_4$ antagonist is of potential benefit in relieving a migraine attack.

Other CNS disorders of interest include schizophrenia, Parkinson's disease and Huntingdon's chorea.

The invention also provides a pharmaceutical composition comprising a compound of formula (IA), or a pharmaceutically acceptable salt thereof, and a pharmaceutically acceptable carrier.

Such compositions are prepared by admixture and are usually adapted for enteral such as oral, nasal or rectal, or parenteral administration, and as such may be in the form of tablets, capsules, oral liquid preparations, powders, granules, lozenges, reconstitutable powders, nasal sprays, suppositories, injectable and infusable solutions or suspensions. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of irritable bowel syndrome, dyspepsia, atrial arrhythmias and stroke, anxiety and/or migraine in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 1000 mg for example 0.5 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated within the aforementioned dosage ranges.

The invention also provides a compound of formula (I) or a pharmaceutically acceptable salt thereof for use as an active therapeutic substance, in particular for use in the treatment of irritable bowel syndrome, gastro-oesophageal reflux disease, dyspepsia, atrial arrhythmias and stroke, anxiety and/or migraine.

The following Example illustrates the preparation of compounds of formula (I), the following Descriptions relate to the preparation of intermediates.

| | | | | | Examples | | | |
|---|---|---|---|---|---|---|---|---|
| | $R_1$ | $R_2$ | r | $R_3$ | $R_4$ | X | Y | Z |
| E1 | H | H | 1 | H | H | O | O | (i) |
| E2 | H | H | 1 | H | H | O | O | (vi) |
| E3 | H | H | 1 | H | H | O | NH | (i) |
| E4 | H | H | 1 | H | H | O | O | (iii) |
| E5 | H | H | 1 | H | H | O | NH | (iii) |
| E6 | H | H | 0 | H | H | O | O | (i) |
| E7 | 3-(CH$_3$)$_2$ | | 1 | H | H | O | O | (i) |
| E8 | H | H | 1 | H | H | S | O | (i) |
| E9 | H | H | 2 | H | H | O | O | (i) |
| E10 | H | H | 1 | H | H | CH$_2$ | O | (i) |
| E11 | H | H | 0 | H | H | CH$_2$ | O | (i) |
| E12 | H | H | 2 | H | H | CH$_2$ | O | (i) |
| E13 | H | H | 0 | H | H | CH$_2$ | NH | (i) |
| E14 | H | H | 0 | H | H | O | NH | (i) |
| E15 | H | H | 1 | H | H | O | O | Bzppm |
| E16 | H | H | 1 | H | H | SO | O | (i) |
| E17 | — | Δ | — | H | H | CH | O | (i) |
| E18 | — | Γ | — | H | H | CH | O | (i) |
| E19 | H | H | 1 | H | H | S | NH | (i) |
| E20 | H | H | 1 | H | H | O | NH | Bzppm |
| E21 | H | H | 1 | H | H | O | NH | ppm |
| E22 | H | H | 1 | H | H | O | NH | nC$_6$H$_{13}$ppm |
| E23 | H | H | 1 | H | H | O | NH | (ii) |
| E24 | H | H | 1 | H | H | O | NH | Etppm |
| E25 | H | H | 1 | H | H | O | NH | MeSO$_2$Etppm |
| E26 | H | H | 1 | H | H | O | NH | (vi) |
| E27 | H | H | 1 | 8-F | H | O | O | (i) |
| E28 | H | H | 1 | 8-F | H | O | NH | (i) |
| E29 | H | H | 1 | H | H | NMe | O | (i) |
| E30 | — | π | — | H | H | S | O | (i) |
| E31 | H | H | 0 | H | H | S | O | (i) |
| E32 | — | θ | — | H | H | S | O | (i) |
| E33 | — | Λ | — | H | H | N | O | (i) |
| E34 | H | H | 0 | H | H | S | NH | (i) |
| E35 | — | θ | — | H | H | S | NH | (i) |
| E36 | H | H | 1 | H | H | NH | O | (i) |
| E37 | H | H | 0 | H | H | O | O | (vi) |
| E38 | H | H | 2 | H | H | O | NH | (i) |
| E39 | H | H | Γ | H | H | N | O | (i) |
| E40 | H | H | 0 | H | H | S | O | (vi) |
| E41 | H | H | 0 | H | H | S | NH | (vi) |
| E42 | — | θ | — | H | H | S | O | (vi) |
| E43 | — | θ | — | H | H | S | NH | (vi) |
| E44 | H | H | 1 | H | H | S | O | (vi) |
| E45 | — | Γ | — | H | H | N | NH | (i) |

-continued

| | $R_1$ | $R_2$ | r | $R_3$ | $R_4$ | X | Y | Z |
|---|---|---|---|---|---|---|---|---|
| E46 | H | H | 1 | H | H | NH | NH | (i) |
| E47 | H | H | 1 | H | H | O | NH | Phprppm |
| E48 | H | H | 1 | H | H | O | NH | Meppm |

Δ— $AR_1R_2$ is —$(CH_2)_2$—CH=
Bz — benzyl
Γ — $AR_1R_2$ is —CH=CH—CH=
ppm — 4-piperidylmethyl
π — $AR_1R_2$ is —C(CH_3)=CH—
aEt — aminoethyl
θ — $AR_1R_2$ is —CH=CH—
Phpr — 3-phenoxypropyl
Λ — $AR_1R_2$ is —C(CH_3)=CH—C(CH_3)=

EXAMPLE 1

(1-$^n$Butyl-4-piperidyl)methyl-3,4-dihydro-2 H-[1,3]oxazino[3,2-a]indole-10-Carboxylate (E1)

a) A suspension of indole-3-carboxylic acid (500 mg, 0.003 mole) in dichloromethane (50 ml) was treated with oxalyl chloride (0.635 g, 0.005 mole) and two drops of dimethylformamide. The mixture was stirred at room temperature for one and a half hours then the solvent was removed in vacuo to leave the acid chloride.

A solution of 1-butyl-4-piperidinemethanol, D6, (513 mg, 0.003 mole) in dry THF (10 ml) under an atmosphere of nitrogen, was cooled in an ice bath. n-Butyllithium (1.88 ml of 1.6M solution in hexane, 0.003 mole) was added dropwise and the resulting solution stirred at 0° C. for 15 minutes.

The acid chloride was dissolved in dry THF (20 ml) and the solution added dropwise to the solution of the lithium alkoxide at 0° C.

The reaction mixture was allowed to warm to room temperature and was stirred for 3 hours. The solvent was removed in vacuo and the residue partitioned between chloroform and water. The chloroform was separated, washed several times with water, dried and concentrated to give (1-butyl-4-piperidyl)methyl-1 H-indole-3-carboxylate as a pale brown gum.

$^1$H NMR (250 MHz) CDCl$_3$;
δ: 9.90 (br s, 1 H), 8.10–8.18 (m, 1 H), 7.78 (d, 1 H), 7.37–7.46 (m, 1 H), 7.16–7.28 (m, 2 H), 4.19 (d, 2 H), 3.05–3.15 (br d, 2 H), 2.40–2.49 (m, 2 H), 0.90 (t, 3 H), 1.20–2.18 (m, 11 H).

b) A suspension of N-chlorosuccinimide (57 mg, 0.48 mmole) in chloroform (2 ml) was treated with a solution of (1-$^n$butyl-4-piperidyl)methyl indole-3-carboxylate (100 mg, 0.32 mmole) in chloroform (2 ml) and the mixture stirred at room temperature for 2 h. The pale yellow solution was treated with 3-bromo-1-propanol (0.03 ml, 0.32 mmole), stirred at room temperature for 16 h; then basified with 10% Na$_2$CO$_3$ solution and extracted with chloroform. The extract was dried and concentrated to leave a yellow gum, which was dissolved in acetone (6 ml), treated with anhydrous potassium carbonate (130 mg, 0.94 mmole) and stirred at room temperature for 18 h. The mixture was treated with 10% Na$_2$CO$_3$ solution and extracted with ethyl acetate. The extract was dried and concentrated to leave a brown oil, which was chromatographed, first on silica gel eluting with chloroform/methanol (97:3), then on basic alumina eluting with ethyl acetate to give a colourless oil. This was crystallised from ether/pentane to afford the title compound (E1) as a white solid (11 mg) mp 117°–119° C.
$^1$H NMR (CDCl$_3$)
δ: 7.97 (d,1 H), 7.10–7.30 (m,3H), 4.55 (t,2H), 4.20 (d,2H), 4.11 (t,2H), 2.90–3.03 (m,2H), 2.25–2.40 (m,4 H), 1.75–2.00 (m,5 H), 1.22–1.55 (m,6 H), 0.91 (t,3 H)
MS (EI) M$^+$370

EXAMPLE 2 eq-Quinolizidin-2-ylmethyl-3,4-dihydro-2 H-[1,3]oxazino[3,2-a]indole-10-Carboxylate (E2)

a) eq-2-Hydroxymethylquinolizidine (N.J. Leonard et al., J. Org. Chem., 1957, 22, 1445) was reacted with indole-3-carboxylic acid chloride using the method described in Example 1a to afford eq-quinolizidin-2-ylmethyl 1-H-indole-3-carboxylate mp 154°–157° C.
$^1$H NMR (CDCl$_3$)
δ: 9.40 (br,s,1 H), 8.10–8.20 (m,1 H), 7.87 (d,1 H), 7.35–7.45 (m,1 H), 7.20–7.30 (m,2 H), 4.20 (d,2 H), 2.80–2.97 (m,2 H), 1.43–2.20 (m,11 H), 1.10–1.40 (m,3 H).

b) eq-Quinolizidin-2-ylmethyl 1 H-indole-3-carboxylate was treated initially with N-chlorosuccinimide (1.5 equivalents) for 2 h, then with 3-bromo-1-propanol (2 equivalents) for 16 h, followed by anhydrous potassium carbonate in acetone, using the method described in Example 1b. The crude product was purified using the same chromatography conditions as in Example 1b to afford the title compound as a colourless oil (51%). This was converted to its hydrochloride salt and crystallised from acetone mp 164°–167° C.
$^1$H NMR (HCl salt) (d$^6$DMSO)
δ: 10.35 (br,s,1 H), 7.85 (d,1 H), 7.32 (d,1 H), 7.07–7.20 (m,2 H), 4.54 (t,2 H), 4.13 (t,2 H), 4.05 (d,2 H), 3.25–3.43 (m,2 H), 2.74–3.15 (m,3 H), 2.20–2.33 (m,2 H), 2.00–2.15 (m,1 H), 1.35–1.95 (m,10 H).

EXAMPLE 3

N-[(1-$^n$Butyl-4-piperidyl)methyl]-3,4-dihydro-2 H-[1,3]oxazino[3,2-a]indole-10-Carboxamide (E3, SB 207266)

Method 1: A stirred solution of N-chlorosuccinimide (57 mg, 0.48 mmole) in chloroform (3 ml) was treated with a solution of N-[(1-$^n$butyl-4-piperidyl)methyl] indole-3-carboxamide, D1, (100 mg, 0.32 mmole) in chloroform (8 ml) and kept at room temperature for 2 h, then treated with 3-bromo-1-propanol (0.03 ml, 0.32 mmole). After stirring for 16 h, more 3-bromo-1-propanol (0.03 ml, 0.32 mmole) was added. The mixture was stirred at room temperature for a further 3 h, then treated with excess 10% Na$_2$CO$_3$ solution and extracted with chloroform. The extract was dried (Na$_2$SO$_4$) and concentrated in vacuo to leave a yellow oil, which was dissolved in acetone (10 ml), treated with anhydrous potassium carbonate (130 mg, 0.96 mmole) and stirred at room temperature for 16 h. The mixture was concentrated in vacuo, the residue treated with 10% Na$_2$CO$_3$ solution (10 ml) and extracted with chloroform. The extract was dried (Na$_2$SO$_4$) and concentrated in vacuo to leave a yellow oil, which was chromatographed, initially on silica gel eluting with chloroform/methanol (19:1), then on basic alumina eluting with ethyl acetate. The colourless oil obtained crystallised from ether to afford the title compound (E3, SB 207266) as a white solid (20 mg, 17%) mp 110°–113° C.
$^1$H NMR (CDCl$_3$)
δ: 8.34 (d,1 H), 7.05–7.30 (m,3 H), 6.55 (t,1 H), 4.53 (t,2 H), 4.10 (t,2 H), 3.33 (t,2 H), 2.90–3.05 (m,2 H), 2.25–2.45 (m,4 H), 1.90–2.25 (m,2 H), 1.20–1.85 (m,9 H), 0.92 (t,3 H).
MS (CI) MH$^+$370.

Method 2: A stirred suspension of N-[(1-"butyl-4-piperidyl)methyl] indole-3-carboxamide (D1, 120 g, 0.38 mole) in chloroform (2 L) under nitrogen at room temperature was treated with freshly distilled 3-bromo-1-propanol (69 ml, 0.77 mole) followed by the portionwise addition of dry N-chlorosuccinimide (55 g, 0.42 mole) over 5 minutes. The resulting yellow solution was stirred for 2.5 h, then treated with 1M HCl in ether (15 ml, 0.015 mole). A moderate exotherm occurred and the reaction colour changed to orange. After a further 2 h the mixture was treated with 10% $Na_2CO_3$ solution (700 ml) and the chloroform layer separated, dried ($Na_2SO_4$) and concentrated in vacuo to leave a thick red oil. This was treated with acetone (1.5 L) and anhydrous potassium carbonate (130 g, 0.95 mole), then stirred at room temperature for 18 h. The reaction mixture was concentrated in vacuo and the residue treated with water (1 L) and extracted with ethyl acetate (1 L). On standing a solid began crystallising from the ethyl acetate extract. After 2 h at 8° C. this was filtered off and dried to afford 51.7 g of the title compound (E3) as a beige solid. The mother liquors were extracted with 1M HCl acid (800 ml), the acid extract then basified with $K_2CO_3$ and extracted with chloroform (2×700 ml). The combined chloroform extracts were dried ($Na_2SO_4$), concentrated in vacuo and the residue chromatographed on silica gel eluting with chloroform/methanol (96:4). A yellow oil was obtained which upon trituration with ether gave a further 21.3 g of title compound (E3) as a white solid. Conversion to the hydrochloride salt and recrystallisation from ethanol/60–80 petrol gave a white solid (SB 207266-A) mp 254°–256° C. dec.

HCl salt—$^1$H NMR ($D_2O$)

δ: 7.90 (d,1 H), 6.88–7.20 (m,3 H), 4.35 (br t,2 H), 3.70 (br t,2 H), 3.40 (br d,2 H), 3.20 (br d,2 H), 2.9 (br t,2 H), 2.65(br t,2 H), 2.12 (br t,2 H), 1.20–1.90 (m,9 H), 0.87 (t,3 H). Elemental analysis obtained was as follows:

|  | Theory | Found |
| --- | --- | --- |
| Carbon | 65.09 | 64.76, 64.75 |
| Hydrogen | 7.95 | 7.73, 7.77 |
| Nitrogen | 10.35 | 10.35, 10.36 |

EXAMPLE 4

2-(1-Piperidyl)ethyl 3,4-dihydro-2 H-[1,3]oxazino [3,2-a]indole-10-Carboxylate (E4)

a) 1-Piperidineethanol was reacted with 1 H-indole-3-carboxylic acid chloride using the method described in Example 1a to afford 2-(1-piperidyl)ethyl 1 H-indole-3-carboxylate.

$^1$H NMR (CDCl$_3$)

δ: 9.6 (br.s, 1 H), 8.03–8.12 (m, 1 H), 7.73 (d, 1 H), 7.30–7.40 (m,1 H), 7.13–7.25 (m, 2 H), 4.48 (t, 2 H), 2.82 (t, 2 H), 2.50–2.65 (m, 4 H), 1.35–1.70 (m, 6 H).

b) 2-(1-Piperidyl)ethyl 1 H-indole-3-carboxylate was treated initially with N-chlorosuccinimide (1.5 equivalents) for 2 h, then with 3-bromo-1-propanol (3 equivalents) for 21 h, followed by anhydrous potassium carbonate in acetone, using the method described in Example 1b. The crude product was purified using the same chromatography conditions as in Example 1b to afford the title compound. (E4) as a pale yellow oil (15%). This was converted to its oxalate salt and crystallised from acetone mp 174°–177° C.

Free base: $^1$H NMR (CDCl$_3$)

δ: 8.02 (d, 1 H), 7.07–7.30 (m,3 H), 4.40–4.55 (m, 4 H), 4.08 (t, 2 H), 2.78 (t, 2 H), 2.45–2.65 (m, 4 H), 2.25–2.38 (m, 2 H), 1.54–1.66 (m, 4 H), 1.35–1.50 (m, 2 H).

MS (CI) MH$^+$329.

EXAMPLE 5

N-[2-(1-Piperidyl)ethyl] 3,4-dihydro-2 H-[1,3] oxazino[3,2-a]indole-10-Carboxamide (E5)

N-[2-(1-Piperidyl)ethyl] 1 H-indole-3-carboxamide (D2) was treated initially with N-chlorosuccinimide, then with 3-bromo-1-propanol, then with potassium carbonate in acetone following the method described in Example 3. The crude product was chromatographed on silica gel eluting with chloroform/methanol (19:1) to give a pale yellow oil, which crystallised from ether to afford the title compound (E5) as a white solid (29%) mp 124°–127° C.

$^1$H NMR (CDCl$_3$)

δ: 8.33 (d, 1 H), 7.06–7.28 (m, 3 H), 7.02 (br.t, NH), 4.51 (t, 2 H), 4.08 (t, 2 H), 3.50–3.60 (m, 2 H), 2.54 (t, 2 H), 2.30–2.60 (m, 6 H), 1.40–1.65 (m, 6 H).

MS (CI) MH$^+$328.

EXAMPLE 6

(1-"Butyl-4-piperidyl)methyl-2,3-dihydrooxazolo[3, 2-a]indole-9-Carboxylate (E6)

(1-"Butyl-4-piperidyl)methyl 1 H-indole-3-carboxylate (Example 1a) was treated initially with N-chlorosuccinimide (1.5 equivalents) for 4 h, then with 2-bromoethanol (2 equivalents) for 18 h, followed by anhydrous potassium carbonate in acetone (18 h), using the method described in Example 1b. The crude product was purified using the same chromatography conditions as in Example 1b to give a colourless oil (26%), which crystallised from ether to afford the title compound (E6) as a white solid mp 128°–130° C.

$^1$H NMR (CDCl$_3$)

δ: 7.95–8.02 (m, 1 H), 7.07–7.27 (m, 3 H), 5.18–5.27 (m, 2 H), 4.24–4.33 (m, 2 H), 4.19 (d, 2 H), 2.92–3.04 (m, 2 H), 2.27–2.38 (m, 2 H), 1.75–2.05 (m, 5 H), 1.25–1.66 (m, 6 H), 0.91 (t, 3 H).

MS (EI) M$^+$356.

EXAMPLE 7

(1-"Butyl-4-piperidyl)methyl-3,3-dimethyl-3,4-dihydro-2 H-[1,3]oxazino[3,2-a]indole-10-Carboxylate (E7)

(1-"Butyl-4-piperidyl)methyl 1 H-indole-3-carboxylate (Example 1a) was treated initially with N-chlorosuccinimide (1.5 equivalents) for 2 h, then with 3- bromo-2,2-dimethyl-1-propanol (2 equivalents) for 20 h, followed by anhydrous potassium carbonate in acetone (2½ days) using the method described in Example 1b. The crude product was chromatographed on silica gel eluting with chloroform/methanol (95:5) to afford the title compound (E7) as a white solid (10%) mp. 134°–135° C.

$^1$H NMR (CDCl$_3$)

δ: 7.98 (d, 1 H), 7.08–7.30 (m, 3 H), 4.21 (d, 2 H), 4.15 (s, 2 H), 3.77 (s, 2 H), 2.95–3.07 (m, 2 H), 2.32–2.42 (m, 2 H), 1.80–2.10 (m, 5 H), 1.25–1.60 (m, 6 H), 1.20 (s, 6 H), 0.93 (t, 3 H).

MS (CI) MH$^+$399.

EXAMPLE 8

(1-"Butyl-4-piperidyl)methyl-3,4-dihydro-2 H-[1,3] thiazino[3,2-a]indole-10-Carboxylate (E8)

(1-"Butyl-4-piperidyl)methyl 1 H-indole-3-carboxylate (Example 1a) (314 mg, 0.0010 mole) was treated initially with N-chlorosuccinimide (180 mg, 0.0015 mole) for 2 h, then with 3-chloro-1-propanethiol (0.20 ml, 0.0020 mole) for 5 days using the method described in Example 1b. The resulting solution was basified with 10% $Na_2CO_3$ solution and extracted with chloroform. The extract was dried ($Na_2SO_4$) and concentrated under vacuum to leave a dark oil which was chromatographed on silica gel eluting with chloroform/methanol (95:5) to afford (1 -"butyl-4-piperidyl) methyl 2-(3-chloropropylmercapto)-1 H-indole-3-carboxylate as a grey oil (220 mg). This was dissolved in acetone (50 ml), treated with anhydrous potassium carbonate (220 mg, 0.0015 mole) and sodium iodide (390 mg, 0.0026 mole) and heated under reflux for 8 h. The mixture was concentrated under vacuum and the residue treated with 10% $Na_2CO_3$ solution, then extracted with ethyl acetate. The extract was dried ($Na_2SO_4$) and concentrated. The residue was chromatographed on basic alumina eluting with ethyl acetate. The colourless oil obtained crystallised from ether to afford the title compound (E8) as a white solid (80 mg, 21%) mp 99°–100° C.
$^1$H NMR ($CDCl_3$)

δ: 7.97–8.04 (m, 1 H), 7.14–7.30 (m, 3 H), 4.22 (d, 2 H), 4.15 (t, 2 H), 3.05–3.15 (m, 2 H), 2.92–3.02 (m, 2 H), 2.38–2.50 (m, 2 H), 2.27–2.37 (m, 2 H), 1.75–2.02 (m, 5 H), 1.20–1.55 (m, 6 H), 0.91 (t, 3 H).
MS (EI) M$^+$386.

EXAMPLE 9

(1-"Butyl-4-piperidyl)methyl-2,3,4,5-tetrahydro[1,3] oxazepino[3,2-a]indole-11-Carboxylate (E9)

(1-"Butyl-4-piperidyl)methyl 1 H-indole-3-carboxylate (Example 1a) was treated initially with N-chlorosuccinimide (1.5 equivalents) for 2 h, then with 4-chloro-1-butanol (2 equivalents) for 18 h using the method of Example 1b and the product isolated as in Example 8 to afford (1 -"butyl-4-piperidyl) methyl 2-(4-chlorobutoxy)-1 H-indole-3-carboxylate as a yellow oil. A solution in acetone was treated with anhydrous potassium carbonate and sodium iodide and heated under reflux for 30 h, then purified as in Example 8 to afford the title compound (E9) as a pale yellow oil (31%). This was converted to its oxalate salt and crystallised from acetone to give a white solid mp 161°–164° C.
Oxalate salt: $^1$H NMR (d$^6$ DMSO) δ: 7.85–7.95 (m, 1 H), 7.45–7.55 (m, 1 H), 7.10–7.25 (m, 2 H), 4.15–4.30 (m, 4 H), 4.10 (d, 2 H), 3.35–3.45 (m, 2 H), 2.80–3.05 (m, 4 H), 1.80–2.10 (m, 7 H), 1.50–1.75 (m, 4 H), 1.20–1.40 (m, 2 H), 0.89 (t, 3 H).
MS (EI) M$^+$384.

EXAMPLE 10

(1-"Butyl-4-piperidyl)methyl 6,7,8,9-tetrahydropyrido[1,2-a]indole-10-Carboxylate (E10)

A solution of 6,7,8,9-tetrahydropyrido[1,2-a]indole-10-carboxylic acid (D3)(400 mg, 0.00186 mole) in dichloromethane (20 ml) was treated with oxalyl chloride (0.20 ml, 0.0023 mole) and 2 drops of DMF and stirred at room temperature for 2 h, then concentrated in vacuo to give the acid chloride as an orange solid.

A solution of (1-"butyl-4-piperidyl)methanol (D6) (0.32 g, 0.00186 mole) in dry THF (25 ml) at 5° C. under nitrogen was treated with 1.5M methyllithium in ether (1.24 ml, 0.00186 mole) and left to stir for 15 minutes, then treated with a solution of the above acid chloride in dry THF)15 ml). After 16 hat room temperature, the mixture was treated with saturated $K_2CO_3$ solution (50 ml) and extracted into ethyl acetate (2×75 ml), dried ($Na_2SO_4$) and concentrated in vacuo. The residue was chromatagraphed on silica gel eluting with chloroform/ethanol (95:5) to afford the title compound (E10) as a yellow oil. This was converted to its hydrochloride salt to afford a white solid. m.p. 230°–232° C. HCl salt: $^1$H NMR (d$^6$DMSO)

δ: 10.3 (br.s, 1 H), 7.92–8.03 (m, 1 H), 7.43–7.53 (m, 1 H), 7.16–7.26 (m, 2 H), 4.18 (d, 2 H), 4.11 (t, 2 H), 3.43–3.56 (m, 2 H), 3.23 (t, 2 H), 2.82–3.05 (m, 4 H), 1.85–2.12 (m, 7 H), 1.60–1.80 (m, 4 H), 1.25–1.40 (m, 2 H), 0.90 (t, 3 H).
MS (EI) M$^+$368.

EXAMPLE 11

(1-"Butyl-4-piperidyl)methyl-2,3-dihydro-1 H-pyrrolo[1,2-a]indole-9-Carboxylate (E11)

The title compound (E11) was prepared from 2,3-dihydro-1 H-pyrrolo[ 1,2-a]indole-9-carboxylic acid (D4) using the method of Example 10, and was isolated as a pale orange solid (24%) m.p. 100°–102° C.
$^1$H NMR ($CDCl_3$)

δ: 8.03–8.12 (m, 1 H), 7.13–7.28 (m, 3 H), 4.17 (d, 2 H), 4.11 (t, 2 H), 3.29 (t, 2 H), 2.95–3.08 (m, 2 H), 2.57–2.72 (m, 2 H), 2.30–2.41 (m, 2 H), 1.92–2.07 (m, 2 H), 1.73–1.90 (m, 3 H), 1.40–1.60 (m, 4 H), 1.22–1.39(m, 2 H), 0.92 (t, 3 H).
MS (EI) M$^+$354.

EXAMPLE 12

(1-"Butyl-4-piperidyl)methyl 7,8,9,10-tetrahydro-6 H-azepino[1,2-a]indole-11-Carboxylate (E12)

The title compound (E12) was prepared from 7,8,9, 10-tetrahydro-6 H-azepino[1,2-a]indole-11-carboxylic acid (D5) using the method of Example 10. The crude product was purified by chromatography on silica gel eluting with chloroform/ethanol (98:2) to give a yellow oil, which was converted to its hydrochloride salt to afford a beige solid (20%) mp 196°–198° C.
$^1$H NMR (d$^6$DMSO)—HCl salt δ: 10.52(br s, 1 H), 7.93–8.00(m,1 H), 7.55–7.62(m,1 H), 7.13–7.25(m,2 H), 4.25-4.40(m,2 H), 4.17(d,2 H), 3.35–3.55 (m,4 H), 2.80–3.1 0(m,4 H), 1.55–2.15(m, 13 H), 1.24–1.40 (m,2 H), 0.88(t,3 H).
MS (CI) MH$^+$383.

EXAMPLE 13

N-[(1-"Butyl-4-piperidyl)methyl]-2,3-dihydro-1 H-pyrrolo[1,2-a]indole-9-Carboxamide (E13)

A solution of 2,3-dihydro-1 H-pyrrolo[1,2-a]indole-9-carboxylic acid (D4) (180 mg, 0.89 mmole) in dichloromethane (20 ml) was treated with oxalyl chloride (0.096 ml, 1.1 mmole) and 2 drops of DMF and stirred at room temperature for 1 h, then concentrated in vacuo to give the acid chloride as a yellow solid.

A solution of (1-"butyl-4-piperidyl)methylamine (prepared as in Description 1), (150 mg, 0.89 mmole) and triethylamine (0.15 ml, 1.1 mmole) in dichloromethane (20 ml) under nitrogen was treated with a solution of the above acid chloride in dichloromethane (5 ml) and stirred at room temperature for 3 h. The solution was treated with 10% $Na_2CO_3$ solution and the organic layer separated, dried ($Na_2SO_4$) and concentrated in vacuo to leave a beige solid. This was recrystallised from ethyl acetate to afford the title compound (E13) as a white solid (180 mg, 55%) mp 152°–154° C.
$^1$H NMR ($CDCl_3$)

δ: 7.75–7.84(m,1 H), 7.13–7.33(m,3 H), 5.93(br t, NH), 4.10(t,2 H), 3.38(t,2 H), 3.31(t,2 H), 2.90–3.02(m,2 H), 2.65(quintet,2 H), 2.28–2.36(m,2 H), 1.60–2.10(m,6 H), 1.22–1.55(m,5 H), 0.90(t,3 H).
MS (CI) MH$^+$354.

EXAMPLE 14

N-[(1-$^n$Butyl-4-piperidyl)methyl]-2,3-dihydrooxazolo[3,2-a]indole-9-Carboxamide (E14)

N-[(1-$^n$Butyl-4-piperidyl)methyl] indole-3-carboxamide (D1) was treated initially with N-chlorosuccinimide (1.5 equivalents) for 2 h, then with 2-bromoethanol (2 equivalents) for 16 h, followed by potassium carbonate (3 equivalents) in acetone for 68 h, using the method described in Example 1b. The crude product was purified by chromatography on silica gel eluting with chloroform/ethanol (19:1) to afford the title compound (E14) as a white solid following recrystallisation from chloroform/ether (14%) mp 156°–158° C.
$^1$H NMR (CDCl$_3$)
δ: 8.19(d,1 H), 7.00–7.30(m,3 H), 6.00(t,NH), 5.15(t,2 H), 4.20(t,2 H), 3.32(t,2 H), 2.90–3.15(m,2 H), 2.25–2.42 (m,2 H), 1.20–2.05(m, 11 H), 0.90(t,3 H). MS(CI) MH$^+$356.

EXAMPLE 15

(1-Benzyl-4-piperidyl)methyl-3,4-dihydro-2 H-[1,3]oxazino[3,2-a]indole-10-Carboxylate (E15)

a) Indole-3-carboxylic acid was converted to its acid chloride and then reacted with 1-benzyl-4-piperidinemethanol (D7) using the method given in Example 1a. The resulting orange oil was chromatographed on silica gel eluting with chloroform/ethanol (9:1) to afford (1-benzyl-4-piperidyl)methyl indole-3-carboxylate as a yellow oil (88%).
$^1$H NMR (CDCl$_3$)
δ: 9.24(s,1 H), 8.12–8.20(m,1 H), 7.81(d,1 H), 7.20–7.45 (m,8 H), 4.20(d,2 H), 3.53(s,2 H), 2.90–3.04(m,2 H), 1.73–2.10(m,5 H), 1.36–1.58(m,2 H).

b) (1-Benzyl-4-piperidyl)methyl indole-3-carboxylate was treated initially with N-chlorosuccinimide (1.5 equivalents) for 2 h, then with 3-bromo-1-propanol (2 equivalents) for 16 h, followed by anhydrous potassium carbonate in acetone, using the method described in Example 1b. The crude product was purified by chromatography on silica gel eluting with chloroform/ethanol (19:1) to afford the title compound (E15) as a beige solid following recrystallisation from chloroform/ether (47%) mp 158°–160° C.
$^1$H NMR (CDCl$_3$)
δ: 7.94–8.00(m,1 H), 7.10–7.38(m,8 H), 4.48–4.56(m,2 H), 4.19(d,2 H), 4.05–4.12(m,2 H), 3.50(s,2 H), 2.88–2.98 (m,2 H), 2.28–2.39(m,2 H), 1.75–2.08(m,5 H), 1.35–1.55 (m,2 H).
MS (CI) MH$^+$405.

EXAMPLE 16

(1-$^n$Butyl-4-piperidyl)methyl-3,4-dihydro-1-oxo-2 H-[1,3]thiazino[3,2-a]indole-10-Carboxylate (E16)

A solution of (1-$^n$butyl-4-piperidyl)methyl 3,4-dihydro-2 H-[1,3]thiazino[3,2-a]indole-10-carboxylate (E8, 80 mg, 0.21 mmole) in acetone (5 ml) and water (5 ml) was treated with sodium periodate (100 mg, 0.46 mmole) and stirred at room temperature for 24 h. The solution was then treated with saturated K$_2$CO$_3$ solution (10 ml) and extracted using ethyl acetate (2×25 ml). The extract was dried (Na$_2$SO$_4$) and concentrated in vacuo to leave a yellow oil, which was chromatographed on silica gel eluting with 5% methanol/chloroform. The colourless oil obtained crystallised from ether to give the title compound (E16) as a white solid (27 mg, 32%) mp 130°–135° C.
$^1$H NMR (CDCl$_3$) δ: 8.24 (d, 1 H), 7.30–7.50 (m, 3 H), 4.54 (dd, 1 H), 4.22–4.38 (m, 2 H), 4.05 (dt, 1 H), 3.40 (dd, 1 H), 3.21 (dq, 1 H), 2.86–3.08 (m, 3 H), 2.30–2.45 (m, 3 H), 1.80–2.10 (m, 5 H), 1.40–1.65 (m, 4 H), 1.20–1.40 (m, 2 H), 0.90 (t, 3 H).
MS (CI) MH$^+$403.

EXAMPLE 17

(1-$^n$Butyl-4-piperidyl)methyl 6,7-dihydropyrido[1,2-a]indole-10-Carboxylate (E17)

The title compound was prepared from 6,7-dihydropyrido[1,2-a]indole-10-carboxylic acid (D8) using the method of Example 10, and chromatographed on silica gel eluting with ethyl acetate to give a yellow solid (18%) mp 62°–62° C. (n-pentane).
$^1$H NMR (CDCl$_3$)
δ: 8.10–8.17 (m, 1 H), 7.42 (dt, 1 H), 7.18–7.33 (m, 3 H), 6.25–6.35 (m, 1 H), 4.22 (d, 2 H), 4.15 (t, 2 H), 2.90–3.05 (m, 2 H), 2.63–2.75 (m, 2 H), 2.29–2.38 (m, 2 H), 1.75–2.04 (m, 5 H), 1.25–1.55 (m. 6 H), 0.91 (t, 3 H).
MS (EI) M$^+$366.

EXAMPLE 18

(1-$^n$Butyl-4-piperidyl)methyl pyrido[1,2-a]indole-10-Carboxylate (E18)

The title compound was prepared from pyrido[1,2-a]indole-10-carboxylic acid (D9) using the method of Example 10 and chromatographed on silica gel eluting with ethyl acetate to give a yellow solid (10%) mp 57°–59° C. (n-pentane).
$^1$H NMR (CDCl$_3$)
δ: 8.35–8.50 (m, 3 H), 7.88 (d, 1 H), 7.48–7.56 (m, 1 H), 7.28–7.40 (m, 2 H), 6.78–6.86 (m, 1 H), 4.30 (d, 2 H), 2.95–3.05 (m, 2 H), 2.30–2.40 (m, 2 H), 1.85–2.05 (m, 5 H), 1.43–1.60 (m, 4 H), 1.25–1.40 (m, 2 H), 0.92 (t, 3 H).
MS (EI) M$^+$364.

EXAMPLE 19

N-[(1-$^n$Butyl-4-piperidyl)methyl]3,4-dihydro-2 H-[1,3]thiazino[3,2-a]indole-10-Carboxamide (E19)

The title compound was prepared from N-[(1-$^n$butyl-4-piperidyl)methyl] indole-3-carboxamide (D1b) using the method of Example 8 as a white solid (7%) mp 141°–142° C.
$^1$H NMR (CDCl$_3$)
δ: 7.70(d,1 H), 7.13–7.30(m,3 H), 6.07(t,1 H), 4.16(t,2 H), 3.38(t,2 H), 3.08(t,2 H), 2.90–3.02(m,2 H), 2.38–2.50(m,2 H), 2.25–2.36(m,2 H), 1.60–2.00(m,5 H), 1.23–1.56(m,6 H), 0.91 (t,3 H).
MS (EI) M$^+$385.

EXAMPLE 20

N-[(1-Benzyl-4-piperidyl)methy] 3,4-dihydro-2 H-[1,3]oxazino[3,2-a]indole-10-Carboxamide (E20)

a) Indole-3-carboxylic acid was converted to its acid chloride and then reacted with (1-benzyl-4-piperidyl)

methylamine (D10) as in the method of Description 1b to afford N-[(1-benzyl-4-piperidyl)methyl] indole-3-carboxamide as a white solid (60%).

¹H NMR (CDCl₃)

δ: 9.90(s,1 H), 7.85–7.95(m,1 H), 7.64(d,1 H), 7.15–7.43 (m,8 H), 6.17(t,1 H), 3.48(s,2 H), 3.37(t,2 H), 2.83–2.98(m,2 H), 1.87–2.08(m,2 H), 1.54–1.82(m,3 H), 1.23–1.50(m,2 H).

b) A stirred suspension of N-[(l-benzyl-4-piperidyl) methyl] indole-3-carboxamide (17.5 g, 0.050 mole) in chloroform (250 ml) was treated with 3-bromo-1-propanol (10.1 ml, 0.11 mole) and N-chlorosuccinimde (8.7 g, 0.065 mole) at room temperature and a clear solution was obtained in 15 minutes. After 1 h the reaction mixture darkened in colour from pale yellow to orange and temperature rose to 38° C. After a further 1 h the reaction mixture was treated with 10% NaHCO₃ solution and the chloroform layer separated, dried (Na₂SO₄) and concentrated in vacuo to leave a yellow oil, which was chromatographed on silica gel eluting with 3% methanol/chloroform. The 2-(3-bromopropoxy)indole intermediate was dissolved in acetone (400 ml), treated with anhydrous potassium carbonate (11 g, 0.80 mole) and stirred at room temperature for 20 h. The reaction mixture was concentrated in vacuo and the residue treated with water (200 ml) and extracted with chloroform (2×250 ml). The combined extracts were dried (Na₂SO₄), concentrated in vacuo and the residue chromatographed on silica gel eluting with 5% methanol/chloroform to afford the title compound (E20) as a pale yellow oil (3.1 g, 15%). This was converted to its oxalate salt and crystallised from acetone as a white solid mp 169°–170° C.

Free base: ¹H NMR (CDCl₃)

δ: 8.32(d,1 H), 7.05–7.38(m,8 H), 6.53(t,1 H), 4.50(t,2 H), 4.08(t,2 H), 3.48(s,2 H), 3.31(t,2 H), 2.83–2.97(m,2 H), 2.27–2.41(m,2 H), 1.54–2.06(m,5 H), 1.25–1.45(m,2 H).

EXAMPLE 21

N-(4-Piperidylmethyl) 3,4-dihydro-2 H-[1,3]oxazino [3,2-a]indole-10-Carboxamide (E21)

A stirred suspension of N-[(1-benzyl-4-piperidyl)methyl] 3,4-dihydro-2 H-[1,3]oxazino[3,2-a]indole-10-carboxamide oxalate salt (E20, 2.25 g, 0.0046 mole) in ethanol (100 ml) and glacial acetic acid (4 ml) was hydrogenated over 10% Pd—C (0.8 g) at atmospheric pressure and 45° C. for 18 h. The mixture was filtered and the filtrate concentrated in vacuo. The majority of the product was in the solid which had been filtered off. This material was shaken with concentrated potassium carbonate solution (50 ml) and chloroform (50 ml) together with the residue from the filtrate. The mixture was filtered, the chloroform layer separated and dried (Na₂SO₄), then concentrated in vacuo to afford the title compound as a white solid (1.52 g, 100%). This was recrystallised from chloroform/60–80 petrol mp 139°–141° C.

¹H NMR (CDCl₃)

δ: 8.32(d,1 H), 7.03–7.30(m,3 H), 6.53(t,1 H), 4.48(t,2 H), 4.05(t,2 H), 3.30(t,2 H), 3.02–3.15(m,2 H), 2.52–2.70(m,2 H), 2.27–2.40(m,2 H), 1.65–1.90(m,4 H), 1.10–1.30(m,2 H).

MS (EI) M⁺313.

EXAMPLE 22

N-[(1-ⁿHexyl-4-piperidyl)methyl] 3,4-dihydro-2 H-[1,3]oxazino[3,2-a]indole-10-Carboxamide (E22)

A solution of N-(4-piperidylmethyl) 3,4-dihydro-2 H-[1,3]oxazino[3,2-a]indole-10-carboxamide (E21, 250 mg, 0.70 mmole) in acetone (12 ml) was treated with 1-bromohexane (0.14 ml, 1.0 mmole) and anhydrous potassium carbonate (280 mg, 2.0 mmole) and stirred at room temperature for 70 h. The mixture was concentrated in vacuo and the residue treated with 10% Na₂CO₃ solution and extracted with chloroform. The extract was dried (Na₂SO₄), concentrated in vacuo and the residue chromatographed on silica gel eluting with 5% methanol/chloroform to give a yellow oil. This was passed through a short plug of basic alumina eluting with ethyl acetate to afford the title compound (E22) as a colourless oil (150 mg, 54%). This was converted to its hydrochloride salt and crystallised from acetone/ether as a white solid mp 170°–171° C.

Free base: ¹H NMR (CDCl₃)

δ: 8.32(d, 1 H), 7.02–7.30(m,3 H), 6.53(t, 1 H), 4.48(t,2 H), 4.04(t,2 H), 3.32(t,2 H), 2.90–3.00(m,2 H), 2.25–2.38 (m,4 H), 1.83–1.96(m,2 H), 1.20–1.81(m,13 H), 0.88(t,3 H).

MS (EI) M⁺397.

EXAMPLE 23

N-[(1-Cyclohexylmethyl-4-piperidyl)methyl] 3,4-dihydro-2 H-[1,3]oxazino[3,2-a]indole-10-Carboxamide (E23)

N-(4-Piperidylmethyl) 3,4-dihydro-2 H-[1,3]oxazino[3,2-a]indole-10-carboxamide (E21) was alkylated with cyclohexylmethyl bromide using the method of Example 22 with a reaction time of 70 h at room temperature followed by 8 h at reflux temperature. The title compound (E23) was obtained as a white solid (31%) which was converted to its hydrochloride salt and crystallised from acetone/ether as a white solid mp 209°–210° C.

HCl salt: ¹H NMR (CD₃OD)

δ: 8.03–8.09(m,1 H), 7.20–7.28(m,1 H), 7.10–7.17(m,2 H), 4.60(t,2 H), 4.15(t,2 H), 3.53–3.65(m,2 H), 3.36(d,2 H), 2.85–3.05(m,4 H), 2.30–2.43(m,2 H), 1.50–2.07(m,11 H), 1.18–1.46(m,3 H), 0.95–1.13(m,2 H).

MS (EI) M⁺409.

EXAMPLE 24

N-[(1-Ethyl-4-piperidyl)methyl] 3,4-dihydro-2 H-[1,3]oxazino[3,2-a]indole-10-Carboxamide (E24)

N-(4-Piperidylmethyl) 3,4-dihydro-2 H-[1,3]oxazino[3,2-a]indole-10-carboxamide (E21) was alkylated with iodoethane using the method of Example 22. The title compound was obtained as a white solid (27%), which was converted to its hydrochloride salt and crystallised from acetone/ethanol/ether as a white solid mp 243°–245° C.

Free base: ¹H NMR (CDCl₃)

δ: 8.34(d,1 H), 7.05–7.28(m,3 H), 6.55(t,1 H), 4.52(t,2 H), 4.07(t,2 H), 3.33(t,2 H), 2.90–3.02(m,2 H), 2.30–2.40(m,4 H), 1.55–1.98(m,5 H), 1.25–1.45(m,2 H), 1.08(t,3 H).

MS (EI) M⁺341.

EXAMPLE 25

N-[(1-(2-Methanesulphonamidoethyl)-4-piperidyl) methyl] 3,4-dihydro-2 H-[1,3]oxazino[3,2-a]indole-10-Carboxamide (E25)

A stirred solution of N-(4-piperidylmethyl) 3,4-dihydro-2 H-[1,3]oxazino[3,2-a]indole-10-carboxamide (E21, 220 mg, 0.70 mmole) in acetonitrile (8 ml) was treated with diisopropylethylamine (0.24 ml, 1.4 mmole) and N-(2-bromoethyl)methanesulphonamide (D14, 160 mg, 0.77 mmole) and the mixture heated under reflux for 2.5 h. The reaction mixture was concentrated in vacuo and the residue chromatographed on silica gel eluting with dichloromethane/methanol/0.88 ammonia solution (200:10:1). The colourless oil obtained was dissolved in chloroform (30 ml) and washed with water (2×20 ml), then dried ($Na_2SO_4$) and concentrated in vacuo. The residue was passed through a short plug of basic alumina eluting with ethyl acetate to afford the title compound as a colourless oil (34 mg, 11%). This was converted to its oxalate salt and crystallised from acetone to give a white solid mp 80°–85° C.
Free base: $^1$H NMR ($CDCl_3$)

δ: 8.32(d,1 H), 7.05–7.30(m,3 H), 6.56(t,1 H), 4.53(t,2 H), 4.08(t,2 H), 3.33(t,2 H), 3.17(t,2 H), 2.95(s,3 H), 2.78–2.92 (m,2 H), 2.50(t,2 H), 2.28–2.44(m,2 H), 1.55–2.10(m,6 H), 1.20–1.45(m,2 H).

EXAMPLE 26

N-(eq-Quinolizidin-2-ylmethyl) 3,4-dihydro-2 H-[1,3]oxazino[3,2-a]indole-10-Carboxamide (E26)

a) eq-Quinolizidin-2-ylmethylamine (D12) was reacted with indole-3-carboxylic acid chloride using the method of Description 1b) to afford N-(eq-quinolizidin-2-ylmethyl) indole-3-carboxamide as a white solid (55%).
$^1$H NMR ($CD_3OD$)

δ: 8.06–8.15(m,1 H), 7.89(s,1 H), 7.39–7.46(m,1 H), 7.10–7.22(m,2 H), 3.27(d,2 H), 2.80–2.95(m,2 H), 2.04–2.23(m,2 H), 1.53–1.98(m,8 H), 1.22–1.48(m,3 H), 0.96–1.15(m,1 H).

b) A stirred suspension of N-(eq-quinolizidin-2-ylmethyl) indole-3-carboxamide (300 mg, 0.94 mmole) in chloroform (16 ml) was treated with 3-bromo-1-propanol (0.17 ml, 1.9 mmole) followed by N-chlorosuccinimide (140 mg, 1.05 mmole) and gave a clear solution inside 30 minutes. After 2 h the mixture was treated with 1M HCl/ether (3 drops) giving a yellow colouration, then after 1.5 h the mixture was treated with excess 10% $NaHCO_3$ solution and the chloroform layer separated, dried ($Na_2SO_4$) and concentrated in vacuo to leave a yellow oil. This was dissolved in acetone (20 ml), treated with anhydrous potassium carbonate (400 mg, 2.9 mmole) and stirred at room temperature for 24 h, then concentrated in vacuo. The residue was treated with 10% $Na_2CO_3$ solution and extracted with chloroform. The extract was dried ($Na_2SO_4$) and concentrated to leave a yellow oil, which was chromatographed on silica gel eluting with 10% methanol/chloroform. The oil obtained was passed through a short plug of basic alumina eluting with ethyl acetate to afford the title compound (E26) as a colourless oil (110 mg, 32%). This was converted to its hydrochloride salt and crystallised from methanol/ether as a white solid mp 243°–247° C.
Free base: $^1$H NMR ($CDCl_3$)

δ: 8.30(d,1 H), 6.98–7.25(m,3 H), 6.51(t,1 H), 4.45(t,2 H), 3.96(t,2 H), 3.20–3.37(m,2 H), 2.78–2.92(m,2 H), 2.20–2.35 (m,2 H), 1.94–2.14(m,2 H), 0.98–1.85(m, 12 H).
MS (CI) MH$^+$368.

EXAMPLE 27

(1-$^n$Butyl-4-piperidyl)methyl 8-fluoro-3,4-dihydro-2 H-[1,3]oxazino[3,2-a]indole-10-Carboxylate (E27)

a) 5-Fluoroindole-3-carboxylic acid chloride was reacted with (1-$^n$butyl-4-piperidyl)methanol (D6) using the method of Example 1a to afford (1-$^n$butyl -4-piperidyl)methyl 5-fluoroindole-3-carboxylate as an orange oil (30%), following flash chromatography on silica gel eluting with 10% ethanol/chloroform.
$^1$H NMR ($CDCl_3$)

δ: 9.95(br s,1 H), 7.82(s,1 H), 7.78(dd,1 H), 7.33(dd,1 H), 7.00(dt,1 H), 4.22(d,2 H), 3.00–3.15(m,2 H), 2.33–2.47(m,2 H), 1.95–2.10(m,2 H), 1.75–1.93(m,3 H), 1.22–1.65(m,6 H), 0.92(t,3 H).

b) (1-$^n$Butyl-4-piperidyl)methyl 5-fluoroindole-3-carboxylate was reacted with N-chlorosuccinimide and 3-bromo- 1-propanol, then with potassium carbonate in acetone using the method of Example 26b to give a pale oil, which was flash chromatographed on silica gel eluting with 10% ethanol/chloroform. This afforded the title compound (E27) as a pale yellow oil (8%), which was converted to its oxalate salt and obtained as a beige solid mp 118°–119° C.
Free base: $^1$H NMR ($CDCl_3$)

δ: 7.64(dd,1 H), 7.04(dd,1 H), 6.87(dt,1 H), 4.55(t,2 H), 4.20(d,2 H), 4.10(t,2 H), 2.96–3.10(m,2 H), 2.28–2.47(m,4 H), 1.77–2.14(m,5 H), 1.25–1.65(m,6 H), 0.92(t,3 H).
MS (CI) MH$^+$389.

EXAMPLE 28

N-[(1-$^n$Butyl-4-piperidyl)methyl] 8-fluoro-3,4-dihydro-2 H-[1,3]oxazino[3,2-a]indole-10-Carboxamide (E28)

a) 5-Fluoroindole-3-carboxylic acid chloride was reacted with (1-$^n$butyl-4-piperidyl)methylamine (Description 1a) as in the method of Description 1b to afford N-[(1-$^n$butyl-4-piperidyl)methyl] 5-fluoroindole-3-carboxamide as an off-white solid (64%).
$^1$H NMR ($CD_3OD$)

δ: 7.92(s,1 H), 7.78(dd,1 H), 7.38(dd,1 H), 6.95(dt,1 H), 3.28(d,2 H), 2.93–3.07(m,2 H), 2.30–2.42(m,2 H), 1.60–1.87(m,5 H), 1.22–1.60(m,6 H), 0.94(t,3 H).

b) N-[(1-$^n$Butyl-4-piperidyl)methyl] 5-fluoroindole-3-carboxamide was reacted with 3-bromo- 1 -propanol and N-chlorosuccinimide, then with potassium carbonate in acetone using the method of Example 26b to give a yellow oil, which was flash chromatographed on silica gel eluting with 20% ethanol/chloroform to afford the title compound as a pale yellow oil (8%). This was converted to its hydrochloride salt, which was obtained as a beige solid mp 90° C. dec.
Free base: $^1$H NMR ($CDCl_3$)

δ: 7.98(dd,1 H), 6.98(dd,1 H), 6.83(dt,1 H), 6.56(t,1 H), 4.56(t,2 H), 4.08(t,2 H), 3.33(t,2 H), 3.05–3.20(m,2 H), 2.30–2.58(m,4 H), 2.10–2.26(m,2 H), 1.25–1.90(m,9 H), 0.92(t,3 H).
MS (CI) MH$^+$388.

EXAMPLE 29

(1-$^n$Butyl-4-piperidyl)methyl 1-methyl-1,2,3,4-tetrahydropyrimido[1,2-a]indole-10-carboxylate (E29)

A solution of (1-$^n$butyl-4-piperidyl)methanol (D6, 1.7 g, 0.010 mole) in dry THF (20 ml) under argon at 10° C. was treated with 1.5M methyllithium in ether (2.7 ml, 0.004 mole) and stirred for 15 minutes, then a solution of methyl 1-methyl-1,2,3,4-tetrahydropyrimido[1,2-a]indole-10-carboxylate (D11, 0.5 g, 0.002 mole) in THF (5 ml) was added and the reaction mixture heated under reflux for 24 h. The mixture was allowed to cool and then treated with 10% $Na_2CO_3$ solution (50 ml) and extracted with ethyl acetate (2×40 ml). The combined extracts were dried ($Na_2SO_4$), concentrated in vacuo and the residue chromatographed on silica gel eluting with 2% methanol/chloroform to afford the title compound (E29) as a colourless oil (0.58 g, 74%). This was converted to its oxalate salt and recrystallised from methanol to afford a white solid mp 186°–187° C.

Free base: $^1$H NMR (CDCl$_3$)

δ: 7.92(d,1 H), 7.00–7.20(m,3 H), 4.17(d,2 H), 3.95(t,2 H), 3.37(t,2 H), 3.28(s,3 H), 2.92–3.03(m,2 H), 2.28–2.38 (m,2 H); 2.12–2.24(m,2 H), 1.80–2.03(m,5 H), 1.23–1.57 (m,6 H), 0.92(t,3 H).
MS (EI) M$^+$383.

EXAMPLE 30

(1-"Butyl-4-piperidyl)methyl 3-methylthiazolo[3,2-a]indole-9-Carboxylate (E30)

The title compound (E30) was prepared from 3-methylthiazolo[3,2-a]indole-9-carboxylic acid (D13) using the method of Example 10. The crude product was purified by chromatography on silica gel eluting with chloroform/methanol (95:5), followed by passage through a short plug of basic alumina eluting with ether to afford a pale yellow oil (35%). This was converted to its oxalate salt and crystallised from methanol to give a white solid mp 224°–226° C.
Free base: $^1$H NMR (CDCl$_3$)

δ: 8.18(d,1 H), 7.77(d,1 H), 7.14–7.42(m,2 H), 6.40(s,1 H), 4.25(d,2 H), 2.92–3.08(m,2 H), 2.73(s,3 H), 2.28–2.40 (m,2 H), 1.75–2.05(m,5 H), 1.20–1.62(m,6 H), 0.92(t,3 H).
MS (CI) MH$^+$385.

EXAMPLE 31

(1-"Butyl-4-piperidyl)methyl-2,3-dihydrothiazolo[3,2-a]indole-9-Carboxylate (E31)

The title compound was prepared from 2,3-dihydrothiazolo[3,2-a]indole-9carboxylic acid (D15) using the method of Example 10. The crude product was purified by chromatography on silica gel eluting with 5% methanol/chloroform to give a yellow oil. This was passed through a plug of basic alumina eluting with ethyl acetate to afford the title compound as a pale yellow oil (31%) which was converted to its oxalate salt and was crystallised from acetone as an off-white solid mp 212°–215° C.
Free base: $^1$H NMR (CDCl$_3$)

δ: 7.98(d,1 H), 7.09–7.26(m,3H), 4.26(t,2 H), 4.20(d,2H), 3.80(t,2 H), 2.94–3.06(m,2 H), 2.30–2.40(m,2 H), 1.73–2.06 (m,5 H), 1.24–1.60(m,6 H), 0.92(t,3 H).

EXAMPLE 32

(1-"Butyl-4-piperidyl)methyl thiazolo[3,2-a]indole-9-Carboxylate (E32)

The title compound (E32) was prepared from thiazolo[3,2-a]indole-9-carboxylic acid (D16) using the method of Example 10. The crude product was purified by chromatography on silica gel eluting with 3% methanol/chloroform to afford a pale purple solid (70%). This was converted to its oxalate salt and recrystallised from methanol to give a light blue solid mp 217°–218° C.
Free base: $^1$H NMR (CDCl$_3$)

δ: 8.18(d,1 H), 7.79(d, 1 H), 7.65(d,1 H), 7.33–7.43(m,1 H), 7.20–7.30(m, 2 H), 6.91(d,2 H), 4.27(d,2 H), 2.95–3.07 (m,2 H), 2.30–2.40(m,2 H), 1.79–2.08(m,5 H), 1.40–1.62 (m,4 H), 1.33(sextet,2 H), 0.92(t,3 H).

EXAMPLE 33

(1-"Butyl-4-piperidyl)methyl 2,4-dimethylpyrimido [1,2-a]indole-10-Carboxylate (E33)

The title compound (E33) was prepared from methyl 2,4-dimethylpyrimido[1,2-]indole- 10-carboxylate (D17) using the method of Example 29. The crude product was purified by chromatography on silica gel eluting with ethyl acetate to afford an orange oil (21%). This was converted to its oxalate salt to give an orange solid mp 195°–198° C.
Oxalate salt: $^1$H NMR (d$^6$DMSO)

δ: 8.45(d,1 H), 8.35(d,1 H), 7.59(t,1 H), 7.41(t,1 H), 6.97(s,1 H), 4.90(br s,2 H), 4.27(d,2 H), 3.38–3.60(m,2 H), 3.14(s,3 H), 3.27–3.04(m,4 H), 2.61(s,3 H), 2.01–2.27(m,3 H), 1.55–1.84(m,4 H), 1.37(sextet,2 H), 0.97(t,3 H).

EXAMPLE 34

N-[(1-"Butyl-4-piperidyl)methyl] 2,3-dihydrothiazolo[3,2-a]indole-9-Carboxamide

The title compound (E34) was prepared from 2,3-dihydrothiazolo[3,2-a]indole-9-carboxylic acid (D15) via its acid chloride using the method of Example 13. The crude product was purified by chromatography on silica gel eluting with 5% methanol/chloroform to afford a yellow solid (63%). This was converted to its oxalate salt and recrystallised from acetone to give a beige solid mp 203°–204° C.
Oxalate salt: $^1$H NMR (d$^6$DMSO)

δ: 7.83–7.92(m,1 H), 7.33–7.45(m,2 H), 7.08–7.18(m,2 H), 4.35(t,2 H), 3.84(t,2 H), 3.35–3.50(m,2 H), 3.18–3.30 (m,2 H), 2.75–3.05(m,4 H), 1.75–1.95(m,3 H), 1.40–1.70 (m,4 H), 1.30(sextet,2 H), 0.88(t,3 H).

EXAMPLE 35

N-[(1-"Butyl-4-piperidyl)methyl] thiazolo[3,2-a] indole-9-Carboxamide (E35)

The title compound (E35) was prepared from thiazolo[3,2-a]indole-9-carboxylic acid (D1 6) via its acid chloride using the method of Example 13. The crude product was purified by chromatography on silica gel eluting with 5% methanol/ chloroform to afford a purple solid (73%). This was converted to its oxalate salt and recrystallised from acetone to give a purple solid mp 205°–207° C.
Oxalate salt: $^1$H NMR (d$^6$DMSO)

δ: 8.49(d,1 H), 8.14(d,1 H), 8.05(d,1 H), 7.54(t,1 H), 7.20–7.40(m,3 H), 3.38–3.50(m,2 H), 3.24–3.35(m,2 H), 2.75–3.05(m,4 H), 1.80–2.00(m,3 H), 1.40–1.70(m,4 H), 1.30(sextet,2 H), 0.88(t,3 H).

EXAMPLE 36

(1-"Butyl-4-piperidyl)methyl 1,2,3,4-tetrahydropyrimido[1,2-a]indole-10-Carboxylate (E36)

The title compound (E36) was prepared from methyl 1,2,3,4-tetrahydropyrimido[1,2-a]indole-10-carboxylate (D18) using the method of Example 29 with a relux time of 140 h. The crude product was purified by chromatography on silica gel eluting initially with ethyl acetate, then with 10% methanol/ethyl acetate to give a yellow solid. This was passed through a plug of basic alumina eluting with ethyl acetate to afford the title compound as a beige solid (23%), which was converted to its oxalate salt and crystallised from acetone as a beige solid mp 190°–194° C.
Free base: $^1$H NMR (CDCl$_3$)

δ: 7.71(br d,1 H), 6.98–7.18(m,3 H), 7.0(br s,1 H), 4.17(d,2 H), 3.98(t,2 H), 3.46–3.57(m,2 H), 2.92–3.06(m,2 H), 2.30–2.40(m,2 H), 2.22(quintet,2 H), 1.75–2.08(m,5 H), 1.23–1.60(m,6 H), 0.92(t,3 H).

EXAMPLE 37 eq-Quinolizidin-2-ylmethyl 2,3-dihydrooxazolo[3,2-a]indole-9-Carboxylate(E37)

A stirred suspension of eq-quinolizidin-2-ylmethyl 1 H-indole-3-carboxylate (E2a, 280 mg, 0.94 mmole) in chloroform (10 ml) was treated with 2-bromoethanol (0.13 ml) followed by N-chlorosuccinimide (135 mg, 1.0 mmole) and kept at room temperature for 2 h. The mixture was then treated with 1M HCl in ether (0.05 ml, 0.05 mmole) and after 2 h the resulting yellow solution was basified by addition of 10% $Na_2CO_3$ solution (10 ml) and extracted with chloroform (2×15 ml). The combined extracts were dried ($Na_2SO_4$) and concentrated in vacuo to leave an orange oil. This was dissolved in acetone (20 ml), treated with anhydrous potassium carbonate (410 mg, 3.0 mmole) and stirred at room temperature for 22 h, then concentrated in vacuo and the residue treated with 10% $Na_2CO_3$ solution (20 mil) and extracted with ethyl acetate (2×20 ml). The combined extracts were dried ($Na_2SO_4$), concentrated in vacuo and the residiue chromatographed on silica gel eluting with 3% methanol/chloroform. The yellow oil obtained (145 mg, 44%) was passed through a plug of basic alumina eluting with ethyl acetate to afford the title compound (E37) which crystallised as a white solid from ethyl acetate/ether mp 153°–155° C.
$^1$H NMR ($CDCl_3$)
δ: 7.95(d,1 H), 7.00–7.25(m,3 H), 5.14(t,2 H), 4.18(t,2 H), 4.15(d,2 H), 2.78–2.96(m,2 H), 1.02–2.18(m,14 H).

EXAMPLE 38

N-[(1-"Butyl-4-piperidyl)methyl] 2,3,4,5-tetrahydro [1,3]oxazepino[3,2-a]indole-11-Carboxamide (E38)

a) A stirred suspension of N-[(1-"butyl-4-piperidyl) methyl] indole-3-carboxamide (Description 1b, 1.0 g, 0.0032 mole) in chloroform (25 ml) was treated with 4-chlorobutanol (0.69 ml, 0.0064 mole) followed by N-chlorosuccinimide (470 mg, 0.0035 mole) and a yellow solution was produced inside 5 minutes. After a further 40 minutes the solution was observed to darken in colour to orange. The mixture was kept at room temperature for a further 1 h then treated with 10% $Na_2CO_3$ solution (30 ml) and extracted with chloroform (2×30 ml). The combined extracts were dried ($Na_2SO_4$) and concentrated in vacuo to afford an orange oil, which was chromatographed on silica gel eluting with 5% methanol/chloroform to give N-[(1-"butyl-4-piperidyl)methyl] 2-(4-chlorobutoxy)indole-3-carboxamide (0.67 g, 50%) as a yellow oil.
$^1$H NMR ($CDCl_3$)
δ:10.7(br s,1 H), 8.23(d,1 H), 7.00–7.32(m,3 H), 6.88(t,1 H), 4.43(t,2 H), 3.48(t,2 H), 3.34(t,2 H), 2.86–3.02(m,2 H), 2.25–2.40(m,2 H), 1.1 8–2.00(m, 15 H), 0.90(t,3 H).

b) A solution of N-[(1-"butyl-4-piperidyl)methyl] 2-(4-chlorobutoxy)indole-3-carboxamide (0.67 g, 0.0016 mole) in acetone (25 ml) was treated with anhydrous potassium carbonate (0.74 g, 0.0054 mole) and sodium iodide (1.34 g, 0.0089 mole) and heated under reflux for 24 h. The mixture was concentrated in vacuo and the residue treated with 10% $Na_2CO_3$ solution (25 ml) and extracted with chloroform (2×30 ml). The combined extracts were dried ($Na_2SO_4$), concentrated in vacuo and the residue chromatographed on silica gel eluting with 5% methanol/chloroform. The colourless oil obtained was passed through a plug of basic alumina eluting with ethyl acetate to afford the title compound (E38) as a white solid (370 mg, 60%). This was converted to its oxalate salt and crystallised from acetone as a white solid mp 210°–211° C.
Free base: $^1$H NMR ($CDCl_3$)
δ: 8.36–8.44(m,1 H), 7.17–7.25(m,3 H), 6.94(t,1 H), 4.30(t,2 H), 4.11–4.20(m,2 H), 3.35(t,2 H), 2.90–3.00(m,2 H), 2.25–2.35(m,2 H), 2.18(quintet,2 H), 1.55–2.02(m,7 H), 1.23–1.55(m,6 H), 0.92(t,3 H).

EXAMPLE 39

(1-"Butyl-4-piperidyl)methyl pyrimido[1,2-a]indole-10-Carboxylate (E39)

The title compound was prepared from methyl pyrimido [1,2-a]indole-10-carboxylate (D19) using the method of Example 29. The crude product was washed at −78° C. with n-pentane and the residue chromatographed on silica gel eluting with 5% methanol/chloroform to afford an orange oil.
$^1$H NMR ($CDCl_3$)
δ: 8.68–8.78(m,2 H), 8.45(d,1 H), 7.87(d,1 H), 7.59(t,1 H), 7.45(t,1 H), 6.77–6.89(m, 1 H), 4.37(d,2 H), 2.90–3.12 (m,2 H), 2.25–2.48(m,2 H), 1.75–2.13(m,5 H), 1.19–1.70 (m,6 H), 0.92(t,3 H).

EXAMPLE 40 eq-Quinolizidin-2-ylmethyl 2,3-dihydrothiazolo[3,2-a]indole-9-Carboxylate (E40)

2,3-Dihydrothiazolo[3,2-a]indole-9-carboxylic acid (D15) was converted to its acid chloride and reacted with eq-2-hydroxymethylquinolizidine using a procedure analogous to that described in Example 10.
Free base: $^1$H NMR ($CDCl_3$)
δ: 8.00(d, 1 H), 7.15–7.30(m,3 H), 4.34(t,2 H), 4.10–4.25 (m,2 H), 3.87(t,2 H), 2.80–3.00(m,2 H), 1.05–2.20(m,14 H).

EXAMPLE 41 eq-Quinolizidin-2-ylmethyl 2,3-dihydrothiazolo[3,2-a] indole-9-Carboxamide (E41)

2,3-Dihydrothiazolo[3,2-a]indole-9-carboxylic acid (D15) is converted to its acid chloride and reacted with eq-quinolizidin-2-ylmethylamine (D12) using a procedure analogous to that described in Description 1b.

EXAMPLE 42 eq-Quinolizidin-2-ylmethyl thiazolo[3,2-a]indole-9-Carboxylate (E42)

Thiazolo[3,2-a]indole-9-carboxylic acid (D16) was converted to its acid chloride and reacted with eq-2-hydroxymethylquinolizidine using a procedure analogous to that described in Example 10 to afford the title compound as a white solid mp 129°–131° C. (ether).
$^1$H NMR ($CDCl_3$)
δ: 8.16(d,1 H), 7.75(d,1 H), 7.61(d,1 H), 7.33–7.42(m,1 H), 7.19–7.30(m,1 H), 6.87(d, 1 H), 4.15–4.32(m,2 H), 2.80–3.00(m,2 H), 1.40–2.18(m, 11 H), 1.08–1.40(m,3 H).

EXAMPLE 43 eq-Quinolizidin-2-ylmethyl thiazolo[3,2-a]indole-9-Carboxamide (E43)

Thiazolo[3,2-a]indole-9-carboxylic acid (D16) is converted to its acid chloride and reacted with eq-quinolizidin-2-ylmethylamine (D12) using a procedure analogous to that described in Description 1b.

EXAMPLE 44 eq-Quinolizidin-2-ylmethyl 3,4-dihydro-2 H-[1,3] thiazino[3,2-a]indole-10-Carboxylate (E44)

3,4-Dihydro-2 H-[1,3]thiazino[3,2-a]indole-10-carboxylic acid was prepared from thioxindole using a procedure analogous to that described in Description 15. This was converted to its acid chloride and reacted with eq-2-hydroxymethylquinolizidine using a procedure analogous to that described in Example 10. Oxalate salt mp 130°–132° C.
Free base: $^1$H NMR (CDCl$_3$)

δ: 7.96–8.04 (m,1 H), 7.13–7.30(m,3 H), 4.05–4.30(m,4 H), 2.90–3.20(m,4 H), 2.35–2.51(m,2 H), 1.20–2.32 (m,14 H).

EXAMPLE 45

(1-"Butyl-4-piperidyl)methyl pyrimido[1,2-a]indole-10-Carboxamide (E45)

a) Benzyl pyrimido[1,2-a]indole-10-carboxylate is prepared using a procedure analogous to that described in Description 19 and then hydrogenated over 10% Pd/C in ethanol to afford pyrimido[1,2-a]indole-10-carboxylic acid.

b) Pyrimido[1,2-a]indole-10-carboxylic acid is converted to its acid chloride and reacted with (1-"butyl-4-piperidyl) methylamine (D1) using the procedure of Description 1b.

EXAMPLE 46

(1-"Butyl-4-piperidyl)methyl 1,2,3,4-tetrahydropyrimido[1,2-a]indole-10-Carboxamide (E46)

a) 2-Chloroindole-3-carboxylic acid (L. Marchetti and A Andreani, Ann. Chim. (Rome), 1973, 63, 681) was converted to its acid chloride and reacted with N-(1-"butyl-4-piperidyl)methylamine (D 1) using the procedure of Description 1b to afford N-[(1-"butyl-4-piperidyl)methyl] 2-chloroindole-3-carboxamide.
$^1$H NMR (CDCl$_3$)

δ: 9.65(s,1 H), 8.10–8.22(m,1 H), 7.10–7.30(m,3 H), 6.48(t,1 H), 3.38(t,2 H), 2.98–3.16(m,2 H), 1.20–2.50(m,13 H), 0.88(t,3 H). b) N-[(1-Butyl-4-piperidyl)methyl] 2-chloroindole-3-carboxamide was reacted with 3-chloropropylamine using a procedure analogous to that described in Description 18 to give the title compound (E46) as a yellow oil.
$^1$H NMR (CDCl$_3$)

δ: 7.55(br s,1 H), 7.28(d,1 H), 6.96–7.20(m,3 H), 5.76(t,1 H), 3.98(t,2 H), 3.44–3.53(m,2 H), 3.37(t,2 H), 2.94–3.08 (m,2 H), 2.30–2.42(m,2 H), 2.20(quintet,2 H), 1.22–2.10(m, 11 H), 0.92(t,3 H).

EXAMPLE 47

N-[(1-(3-Phenoxypropyl)-4-piperidinyl)methyl] 3,4-dihydro-2 H-[1,3]oxazino[3,2-a]indole-10-Carboxamide A stirred solution of N-(4-piperidinylmethyl) 3,4-dihydro-2 H-[1,3]oxazino[3,2-a]indole-10-carboxamide (E21) (250 mg, 0.80 mmole) and triethylamine (0.25 ml, 1.8 mmole) in a mixture of acetonitrile (15 ml) and N,N-dimethylformamide (10 ml) was treated with 3-phenoxypropyl bromide (0.13 ml, 0.88 mmole) and the solution heated under reflux for 48 h. The mixture was allowed to cool, then concentrated in vacuo and the residue dissolved in ethyl acetate (25 ml) and washed with water (20 ml). The organic solution was dried (MgSO$_4$), concentrated in vacuo and the residue purified by flash chromatography on silica gel eluting with 0– 20% methanol/ethyl acetate to afford the title compound as a pale pink solid after trituation with ether (44 mg) mp 120°–126° C.
$^1$H NMR (CDCl$_3$)

δ: 8.30(d,1 H), 7.07–7.37(m,5 H), 6.96(t,1 H), 6.88(d,2 H), 6.64(t,1 H), 4.57(t,2 H), 4.13(t,2 H), 4.30(t,2 H), 3.22–3.43(m,4 H), 2.78–3.00(m,2 H), 2.13–2.57(m,6 H), 1.59–2.03(m,5 H).

EXAMPLE 48

N-[(1-Methyl-4-piperidyl)methyl]-3,4-dihydro-2 H-[1,3]oxazino[3,2-a]indole-10-Carboxamide (E48)

N-[(1-Methyl-4-piperidyl)methyl] indole-3-carboxamide was prepared from indole-3-carboxylic acid and N-(1-methyl-4-piperidyl)methylamine using an analogous method to Description 1b and then converted to the title compound using an similar procedure to Example 3 (method 2).
$^1$H NMR (CDCl$_3$)

δ: 8.31(d,1 H), 7.26–7.00(m,3 H), 6.54(t,1 H), 4.48(t,2 H), 4.02(t,2 H), 3.33(t,2 H), 2.92–2.80(m,2 H), 2.38–2.20(m,2 H), 2.25(s,3 H), 1.98–1.84(m,2 H), 1.82–1.70(m,2 H), 1.68–1.50(m,1 H), 1.44–1.24(m,2 H).

DESCRIPTIONS

Description 1 (Intermediates for Examples 3, 13, 14, 19 and 28)

a) N-(1-"Butyl-4-piperidyl)Methylamine

A stirred solution of isonipecotamide (70 g, 0.55 mole) and 1-bromobutane (58.8 mil, 0.55 mole) in ethanol (700 ml) was treated with anhydrous potassium carbonate (152 g, 1.10 mole) and heated underreflux for 3 h. The mixture was allowed to cool, then filtered and the filtrate concentrated under vacuum. The residual oil was dissolved in chloroform (400 ml) and washed with water (1×300 ml), then dried (Na$_2$SO$_4$) and concentrated under vacuum to leave a yellow oil (77.5 g). This oil was mixed thoroughly with phosphorus pentoxide (75 g) and the mixture heated at 160°–180° C. under nitrogen for 2.5 h with gentle stirring. The reaction mixture was allowed to cool, then treated with water (500 ml). When the solid mass had dissolved, the solution was basified by addition of solid K$_2$CO$_3$ and extracted with ethyl acetate (2×400 mil). The combined extracts were dried (Na$_2$SO$_4$) and concentrated in vacuo to leave a brown oil (78 g). This was dissolved in dry ether (400 ml) and added dropwise over 30 minutes to a stirred suspension of lithium aluminium hydride (25 g, 0.66 mole) in ether (200 ml) at 0° C. under nitrogen. When addition was complete, the mixture was allowed to warm upto room temperature and stir for 18 h. It was re-cooled to 0° C. and treated cautiously with water (25 ml), 10% NaOH solution (25 ml) and water again (75 ml). The mixture was filtered through kieselguhr and the filtrate concentrated in vacuo to leave a brown oil, which was distilled under vacuum to afford the title compound as a colourless oil (66 g, 71%) bp 96°–99° C. at 3 mm Hg.
$^1$H NMR (CDCl$_3$)

δ: 2.90–3.02(m,2 H), 2.58(d,2 H), 2.25–2.38(m,2 H), 1.65–2.00(m,4 H), 1.08–1.58(m,9 H), 0.92(t,3 H).

b) N-[(1-"Butyl-4-piperidyl)methyl] indole-3-Carboxamide

To a stirring solution of indole-3-carboxylic acid (1 g) in dichloromethane (20 ml) at 0° C. under nitrogen was added oxalyl chloride (0.81 ml) and dry dimethylformamide (3 drops). After 3 hours, the solvents were evaporated under reduced pressure. A portion of the residual acid chloride (420 mg) was dissolved in dichloromethane (12 ml) and added dropwise to a solution of N-(1-ⁿbutyl-4-piperidyl)methylamine (400 mg) in dichloromethane (12 ml) followed by triethylamine (0.36 ml). After stirring at ambient temperature overnight, the reaction mixture was washed with saturated $NaHCO_3$, and the organic phase was dried ($Na_2SO_4$). The solvent was evaporated under reduced pressure and the residue recrystallised from ethyl acetate to give the title compound (D1) (467 mg, 64%).
$^1$H NMR ($CDCl_3$) 250 MHz
δ: 9.29 (br s,1 H), 8.05–7.9 (m,1 H), 7.81 (d,1 H), 7.55–7.4 (m,1 H), 7.39–7.2 (m,2 H), 6.28 (br s,1 H), 3.39 (t,2 H), 3.0 (br d,2 H), 2.45–2.25 (m,2 H), 2.1–1.1 (m,11 H), 0.9 (t,3 H).

Description 2 (Intermediate for Example 5)

N-[2-(1-Piperidyl)ethyl] 1 H-indole-3-Carboxamide

1-Piperidineethylamine was reacted with 1 H-indole-3-carboxylic acid chloride using the method described in Description 1 to afford the title compound (D2) as a beige solid.
$^1$H NMR ($CDCl_3$)
δ: 9.90 (br.s, 1 H), 7.97–8.07 (m, 1 H), 7.78 (d, 1 H), 7.36–7.50 (m, 1 H), 7.15–7.30 (m, 2 H), 7.13 (br.t, NH), 3.55–3.68 (m, 2 H), 2.60 (t,2 H), 2.40–2.55 (m, 4 H), 1.40–1.73 (m, 6 H).

Description 3 (Intermediate for Example 10)

a) Ethyl 2-Aminophenylacetate

A solution of ethyl 2-nitrophenylacetate (13.6 g, 0.065 mole) in ethanol (150 ml) was hydrogenated over 10% Pd/C catalyst (1 g) at room temperature and pressure for 18 hours. The reaction mixture was filtered through keiselgühr and concentrated in vacuo to afford the title compound as a clear oil, which solidified on standing (10.8 g, 93%).
$^1$H NMR ($CDCl_3$)
δ: 7.05–7.15 (m, 2 H), 6.68–6.80 (m, 2 H), 4.13 (q, 2 H), 4.05 (br.s, 2 H), 3.55 (s, 2 H), 1.25 (t, 3 H).

b) Ethyl 2-(5-chlorovalerylamino)Phenylacetate

A solution of ethyl 2-aminophenylacetate (5.60 g, 0.031 mole) and diisopropylethylamine (7.08 ml, 0.042 mole) in dry THF (75 ml) was treated with 5 chlorovaleryl chloride (4.00 ml, 0.031 mole) and left to stir for 1 h. The reaction mixture was concentrated in vacuo and the residue dissolved in ethyl acetate (200 ml) and washed with 1M HCl (100 ml), dried ($Na_2SO_4$) and concentrated in vacuo to afford a beige solid. This was washed with n-pentane/ether (1:1) and dried to afford the title compound as a light beige solid (8.1 g, 91%).
$^1$H NMR ($CDCl_3$)
δ: 8.90 (br.s, 1 H), 7.88 (d, 1 H), 7.05–7.37 (m, 3 H), 4.17 (q, 2 H), 3.60(s, 2 H), 3.45–3.65 (m, 2 H) 2.35–2.55 (m, 2 H), 1.68–1.98 (m, 4 H), 1.28 (t, 3 H).

c) Ethyl 6,7,8,9-tetrahydropyrido[1,2-a]indole-10-Carboxylate

A solution of ethyl 2-(5-chlorovalerylamino) phenylacetate (8.10 g, 0.027 mole) in dry THF (50 ml) was added to a stirred suspension of potassium t-butoxide (7.62 g, 0.068 mole) in dry THF (200 ml) at room temperature under nitrogen. After 1 h the purple solution produced was treated with water (10 ml) and concentrated in vacuo. The residue was shaken with ethyl acetate (200 ml) and sat.ammonium chloride solution (150 ml), then the organic layer separated, dried ($Na_2SO_4$) and concentrated in vacuo to afford an orange oil. This was chromatographed on silica gel eluting with ether to afford the title compound as a yellow solid (1.25 g, 20%).
$^1$H NMR ($CDCl_3$)
δ: 8.07–8.17 (m, 1 H), 7.13–7.30 (m, 3 H), 4.38 (q, 2 H), 4.00 (t, 2 H), 3.30 (t,2 H), 1.82–2.12 (m, 4 H), 1.43 (t, 3 H).

d) 6,7,8,9-Tetrahydropyrido[1,2-a]indole-10-carboxylic Acid

A solution of ethyl 6,7,8,9-tetrahydro-1 H-pyrido[1,2-a]indole-10-carboxylate (1.20 g, 0.0047 mole) in ethanol (50 ml) and 10% NaOH solution (50 ml) was heated under reflux for 4 hours. The reaction was then acidified with 1M HCl acid (50 ml) and extracted with ethyl acetate (50 ml). The organic layer was separated and extracted with 10% $Na_2CO_3$ solution (120 ml) and the aqueous solution then re-acidified with 5M HCl acid and extracted into ethyl acetate (2×75 ml). The organic extracts were combined, dried ($Na_2SO_4$) and concentrated in vacuo to afford the title compound (D3) as a white solid (400 mg, 40%).
$^1$H NMR ($CDCl_3$)
δ: 8.23 (d, 1 H), 7.20–7.35 (m, 3 H), 4.10 (t, 2 H), 3.40 (t, 2 H), 2.00–2.15 (m, 2 H) 1.85–2.00 (m, 2 H).

Description 4 (Intermediate for Examples 11 and 13)

a) Ethyl 2-(4-chlorobutyrylamino)Phenylacetate

The title compound was prepared from ethyl 2-aminophenylacetate using the method of Description 3b,and was isolated as a beige solid, (100%).
$^1$H NMR ($CDCl_3$)
δ: 8.90 (br.s, 1 H), 7.85 (d, 1 H), 7.05–7.35 (m, 3 H), 4.15(q, 2 H), 3.68 (t,2 H), 3.60(s, 2 H), 2.60 (t, 2 H), 2.10–2.30 (m, 2 H), 1.26 (t, 3 H).

b) Ethyl 2,3-dihydro-1 H-pyrrolo[1,2-a]indole-9-Carboxylate

The title compound was prepared from ethyl 2-(4-chlorobutyrylamino)phenylacetate using the method of Description 3c, and was isolated as an orange oil that crystallized on standing (15%).
$^1$H NMR ($CDCl_3$)
δ: 8.05–8.15 (m, 1 H), 7.15–7.30 (m, 3 H), 4.35 (q, 2 H), 4.06 (t, 2 H), 3.28 (t, 2 H), 2.55–2.72 (m, 2 H), 1.40 (t, 3 H).

c) 2,3-Dihydro-1 H-pyrrolo[1,2-a]indole-9-carboxylic Acid

The title compound (D4) was prepared from ethyl 2,3-dihydro- 1 H-pyrrolo[1,2-a]indole-9-carboxylate using the method of Description 3d, and was isolated as an off white solid (42%).
$^1$H NMR ($d^6$DMSO)
δ: 11.85 (br.s, 1 H), 7.90–8.02 (m, 1 H), 7.32–7.47 (m, 1 H), 7.10–7.25 (m, 2 H), 4.15 (t, 2 H), 3.20(t, 2 H), 2.50–2.70 (m, 2 H).

Description 5 (Intermediate for Example 12)

a) Ethyl 2-(6-chlorohexanoylamino)Phenylacetate

The title compound was prepared from ethyl 2-aminophenylacetate and 6-bromohexanoyl chloride using the method of Description 3b and was isolated as a beige solid (100%).
$^1$H NMR ($CDCl_3$)

δ: 8.90(br s, 1 H), 7.90(d,1 H), 7.05–7.35(m,3 H), 4.17 (q,2 H), 3.60(s,2 H), 3.42(t,2 H), 2.45(t,2 H), 1.45–2.00(m,6 H), 1.28(t,3 H).

b) Ethyl 7,8,9,10-tetrahydro-6 H-azepino[1,2-a]indole-11-Carboxylate

The title compound was prepared from ethyl 2-(6-chlorohexanoylamino)phenylacetate using the method of Description 3c, and was purified by chromatography on silica gel eluting with 60–80 petrol/ether (9:1) to afford a white solid (16%).

$^1$H NMR (CDCl$_3$)

δ: 8.07–8.19(m,1 H), 7.15–7.35(m,3 H), 4.40(q,2 H), 4.15–4.25(m,2 H), 3.45–3.60(m,2 H), 1.67–2.00(m,6 H), 1.45(t,3 H).

c) 7,8,9,10-Tetrahydro-6 H-azepino[1,2-a]indole-11-carboxylic Acid

The title compound (D5) was prepared from ethyl 7,8,9,10-tetrahydro-6 H-azepino[1,2-a]indole-1 1-carboxylate by hydrolysis with sodium hydroxide as in the method of Description 3d. After 4 hours heating under reflux, the mixture was acidified with 5M HCl acid and the white solid formed filtered off and dried (82%).

$^1$H NMR (d$^6$DMSO)

δ: 12.05(s,1 H), 7.94–8.04(m,1 H), 7.48–7.60(m,1 H), 7.05–7.20(m,2 H), 4.24–4.36(m,2 H), 3.38–3.53(m,2 H), 1.54–1.90(m,6 H).

Description 6 (Intermediate for Examples 1, 10, 27 and 29)

(1-$^n$Butyl-4-piperidinyl)Methanol

A mixture of ethyl isonipecotate (102 g, 0.65 mole) and 1-bromobutane (72 ml, 0.67 mole) in ethanol (1.2 L) was treated with anhydrous potassium carbonate (180 g, 1.3 mole) and heated under reflux for 2 h. The mixture was allowed to cool and then filtered through kieselguhr. The filtrate was concentrated in vacuo to leave a yellow oil, which was dissolved in ether (300 ml) and added dropwise over 20 minutes to a stirred suspension of lithium aluminium hydride (50 g, 1.3 mole) in either (500 ml) at 0° C. under nitrogen. The mixture was stirred at room temperature for 18 h, then cooled to 0° C. and treated with water (50 ml), 10% NaOH solution (50 ml) and water (50 ml). The mixture was filtered through kieselguhr and the filtrate concentrated under vacuum to leave a pale yellow oil, which was distilled to afford the title compound as a colourless oil (88.5 g, 80%) bp 102°–108° C. at 0.1 mm Hg.

$^1$H NMR (CDCl$_3$)

δ: 3.48(d,2 H), 2.88–3.03(m,2 H), 2.25–2.38(m,2 H), 2.10(br s, 1 H), 1.66–2.00(m,4 H), 1.17–1.60(m,7 H), 0.90(t,3 H)

Description 7 (Intermediate for Example 15)

(1-Benzyl-4-piperidyl)Methanol

Ethyl isonipectoate was intially alkylated with benzyl bromide and the product reduced with lithium aluminium hydride using the method of Description 6, to afford the title compound (D7) as a colourless oil (100%).

$^1$H NMR (CDCl$_3$)

δ: 7.20–7.35(m,5 H), 3.52(s,2 H), 3.48(d,2 H), 2.86–3.00 (m,2 H), 1.20–2.05(m,8 H).

Description 8 (Intermediate for Example 17)

6,7-Dihydropyrido[1,2-a]indole-10-carboxylic Acid

A stirred solution of methyl 6,7-dihydropyrido[1,2-a]indole-10-carboxylate (T. Teitei and L. K. Dalton, Australian J. Chem 1969, 22, 997) (1.0 g, 0.0044 mole) in methanol (40 ml) was treated with a solution of potassium hydroxide (3.0 g, 0.054 mole) in water (50 ml) and heated under reflux for 3 h. The solution was allowed to cool, then acidified with HCl acid and extracted with ethyl acetate. The extract was dried (Na$_2$SO$_4$) and concentrated under vacuum to leave the title compound (D8) as a yellow solid (600 mg, 64%).

$^1$H NMR (CDCl$_3$)

δ: 8.18–8.22 (m, 1 H), 7.50 (d, 1 H), 7.20–7.35 (m,3 H), 6.27–6.38 (m, 1 H), 4.15 (t, 2 H), 2.62–2.78 (m, 2 H).

Description 9 (Intermediate for Example 18)

Pyrido[1,2-a]indole-10-carboxylic Acid

The title compound (D9) was prepared from methyl pyrido[1,2-a]indole-10-carboxylate (T. Teitei and L. K. Dalton, Australian J. Chem. 1969, 22, 997) using the method of Description 8 as a bright yellow solid (76%).

$^1$H NMR (CDCl$_3$ +CD$_3$OD)

δ: 8.56(d, 1 H), 8.34–8.46 (m, 2 H), 7.93 (d,1 H), 7.32–7.57 (m, 3 H), 6.87 (t, 1 H).

Description 10 (Intermediate for Example 20)

(1-Benzyl-4-piperidyl)Methylamine(D 10)

Isonipecotamide was initially alkylated with benzyl bromide, then the amide dehydrated with phosphorus pentoxide and the resulting nitrile reduced with lithium aluminium hydride using the method of Description 1a to afford the title compound as a colourless oil after distillation (67%) bp 106° C. at 0.25 mmHg.

$^1$H NMR (CDCl$_3$)

δ: 7.20–7.37(m,5 H), 3.48(s,2 H), 2.85–2.95(m,2 H), 2.55(d,2 H), 1.87–2.00(m,2 H), 1.60–1.75(m,2 H), 1.10–1.40(m,5 H).

Description 11 (Intermediate for Example 29)

a) Methyl 2-chloroindole-3-Carboxylate

A stirred suspension of methyl indole-3-carboxylate (6.0 g, 0.034 mole) in chloroform (200 ml) was treated with N-chlorosuccinimide (5.04 g, 0.038 mole) to afford a clear solution within 15 minutes. After 2 h at room temperature this was treated with 1M HCl/ether (34 ml, 0.034 mole) and allowed to stir for a further 1 h, then treated with excess 10% Na$_2$CO$_3$ solution and the chloroform layer separated, dried (Na$_2$SO$_4$) and concentrated in vacuo. The residual yellow solid was recrystallised from chloroform/60–80 petrol to afford the title compound (D 11a) as a beige solid (3.4 g, 48%).

$^1$H NMR (CDCl$_3$/d$^6$DMSO)

δ: 11.3(br s,1 H), 8.02–8.12(m,1 H), 7.30–7.40(m,1 H), 7.18–7.26(m,2 H), 3.95(s,3 H).

MS (EI) M$^+$209 and 211.

b) Methyl 1-methyl-1,2,3,4-tetrahydropyrimido[1,2-a]indole-10-Carboxylate

A solution of methyl 2-chloroindole-3-carboxylate (3.4 g, 0.016 mole) in dry THF (70 ml) at 5° C. under nitrogen was treated portionwise with sodium hydride (480 mg of 80% oil dispersion, 0.016 mole) and then stirred at room temperature for 30 mins. The resulting solution was treated with a solution of 3,3-dimethylaminopropyl chloride (0.020 mole) in toluene (30 ml) and heated under reflux for 48 h, then concentrated in vacuo and the residue treated with 10% Na$_2$CO$_3$ solution (50 ml) and extracted with ethyl acetate (2×70 ml). The combined extracts were dried (Na$_2$SO$_4$) and concentrated in vacuo to leave a yellow oil, which was chromatographed on silica gel eluting with ether/60–80 petrol (1:1). The title compound (D11) was obtained as a beige solid (1.95 g, 50%).
$^1$H NMR (CDCl$_3$)
δ: 7.92(d,1 H), 6.97–7.19(m,3 H), 3.92(t,2 H), 3.88(s,3 H), 3.36(t,2 H), 3.27(s,3 H), 2.10–2.22(m,2 H).

Description 12 (Intermediate for Example 26)

eq-Quinolizidin-2-ylmethylamine

A stirred suspension of lithium aluminium hydride (400 mg, 0.010 mole) in THF (20 ml) at room temperature under nitrogen was treated with a solution of eq-2-cyanoquinolizidine (E. Koshinaka et al, Yakugaku Zasshi 1980, 100, 88) in THF (3 ml) and the mixture then heated under reflux for 20 minutes. The mixture was allowed to cool then treated cautiously with water (0.4 ml), 10% NaOH solution (0.4 ml) and water (1.2 ml). The resulting mixture was filtered and the filtrate concentrated in vacuo. The residue was distilled in a Kugelrohr apparatus to afford the title compound (D13) as a colourless oil (700 mg, 97%).
$^1$H NMR (CDCl$_3$)
δ: 2.80–2.92(m,2 H), 2.57(d,2 H), 1.94–2.12(m,2 H), 1.20–1.80(m, 13 H), 0.88–1.05(m,1 H).

Description 13 (Intermediate for Example 30)

3-Methylthiazolo[3,2-a]indole-9-carboxylic Acid a) A stirred solution of 3-methylthiazolo[3,2-a]indole (A. Kiprianov and V. Khilya, Zh. Organ. Khim. 1966, 2, 1474) (270 mg, 0.0014 mole) in DMF (3 ml) was cooled to 5° C. under argon and treated with triflouroacetic anhydride (0.23 ml, 0.0017 mole), then allowed to warm to room temperature over 3 h. The solution was poured into water (25 ml) and the mixture extracted with ethyl acetate (2×20 ml). The combined extracts were dried (Na$_2$SO$_4$) and then concentrated in vacuo to afford 3-methyl-9-trifluoroacetylthiazolo[3,2-a]indole (370 mg, 90%) as a brown solid.
$^1$H NMR (CDCl$_3$)
δ: 8.10(br s,1 H),7.85(d,1 H), 7.39–7.47(m,1 H), 7.25–7.35(m,1 H), 6.69(s,1 H), 2.83(s,3 H).

b) 3-Methyl-9-trifluoroacetylthiazolo[3,2-a]indole (370 mg, 0.0013 mole) was treated with 20% NaOH solution (15 ml) and ethanol (15 ml) and heated under reflux for 6 h. The mixture was concentrated in vacuo to half its volume and the residue acidified with 2M HCl acid and then extracted with ethyl acetate (2×30 ml). The combined extracts were dried (Na$_2$SO$_4$) and concentrated in vacuo to afford the title compound (D13) as a brown solid (300 mg, 100%).
$^1$H NMR (d$^6$DMSO)
δ: 12.3(v br s, 1 H),7.93–8.08(m,2 H), 7.16–7.40(m,2 H), 6.95(s, 1 H), 2.59(s,3 H).

Description 14 (Intermediate for Example 25)

N-(2-Bromoethyl)Methanesulphonamide

A stirred solution of 2-bromoethylamine hydrobromide (5.10 g, 0.025 mole) and triethylamine (6.96 g, 0.050 mole) in dichloromethane (200 ml) at ice bath temperature was treated dropwise with methanesulphonyl chloride (1.96 ml, 0.025 mole). The mixture was allowed to warm to room temperature and stir for 16 h, then washed with water and 5M HCl acid, dried (Na$_2$SO$_4$) and concentrated in vacuo to afford the title compound (D 14) as a colourless oil which solidified on standing to give a white solid (3.5 g, 69%).
$^1$H NMR (CDCl$_3$)
δ: 4.92(s, 1 H), 3.62–3.48(m,4 H), 3.05(s,3 H).

Description 15 (Intermediate for Example 31)

a) 2,3-Dihydrothiazolo[3,2-a]Indole

A solution of thioxindole (400 mg, 0.0027 mole) and 1,2-dibromoethane (0.24 ml, 0.0027 mole) in dry THF (10 ml) was added to a stirred solution of potassium t-butoxide (760 mg, 0.0068 mole) in dry THF (40 ml) at room temperature under argon. The mixture was stirred for 3 h, then treated with water (100 ml) and extracted with ethyl acetate (2×70 ml). The combined extracts were dried (Na$_2$SO$_4$) and concentrated in vacuo to leave an orange oil, which was chromatographed on silica gel eluting with 10% ether/60–80 petrol. The title compound was obtained as a white solid (135 mg, 29%).
$^1$H NMR (CDCl$_3$)
δ: 7.42–7.23(m,1 H), 7.00–7.25(m,3 H), 6.20(s,1 H), 4.23(t,2 H), 3.79(t,2 H). b) 2,3-Dihydrothiazolo[3,2-a]indole-9-carboxylic acid 2,3-Dihydrothiazolo[3,2-a]indole was treated with trifluoroacetic anhydride using the method of Description 13a to afford 9-trifluoroacetylthiazolo[3,2-a]indole as a purple solid (85%).
$^1$H NMR (CDCl$_3$)
δ: 7.93(br s,1 H), 7.07–7.30(3 H), 4.30(t,2 H), 3.85(t,2 H).
The title compound (D15b) was prepared from 9-trifluoroacetyl-2,3-dihydrothiazolo[3,2-a]indole using the method of Description 13b to give a purple solid (95%), which was used without purification.

Description 16 a) Thiazolo[3,2-a]Indole

A stirred solution of thioxindole (3.8 g, 0.025 mole) and bromoacetaldehyde diethyl acetal (3.9 ml, 0.026 mole) in acetone (200 ml) was treated with anhydrous potassium carbonate (6.9 g, 0.050 mole) and the mixture heated under reflux for 2 h followed by 12 h at room temperature. The mixture was concentrated in vacuo and the residue treated with water (100 ml) and extracted with ethyl acetate (2×100 ml). The combined extracts were dried (Na$_2$SO$_4$), concentrated in vacuo and the residue chromatographed on silica gel eluting with 10% ether/60–80 petrol to afford 2-(2,2-diethoxyethylmercapto)indole (3.0 g, 44%) as a yellow oil.
$^1$H NMR (CDCl$_3$)
δ: 9.30(br s,1 H), 7.52(d,1 H), 7.28(d,1 H), 7.04–7.20(m,2 H), 6.58(s,1 H), 4.72(t,1 H), 3.55–3.85(m,4 H), 3.05(d,2 H), 1.31(t,6 H).

A well stirred mixture of 2-(2,2-diethoxyethylmercapto)indole (1.5 g, 0.0057 mole) in polyphosphoric acid (30 g) was heated to 130° C. for 20 minutes, then allowed to cool to room temperature and the mixture diluted with water (300 ml). The resulting aqueous solution was basified by addition of solid potassium carbonate and then extracted with ethyl acetate (2×120 ml). The combined extracts were dried (Na$_2$SO$_4$), concentrated in vacuo and the residue chromatographed on silica gel eluting with 10% ether/60–80 petrol to afford the title compound as a white solid (0.56 g, 57%).
$^1$H NMR (CDCl$_3$)
δ: 7.60–7.70(m,3 H), 7.11–7.28(m,2 H), 6.60(d,1 H), 6.53(s,1 H).

b) Thiazolo[3,2-a]indole-9-carboxylic Acid

Thiazolo[3,2-a]indole was treated with trifluoroacetic anhydride using the method of Description 13a to afford 9-trifluoroacetylthiazolo[3,2-a]indole as a beige solid (95%).

¹H NMR (CDCl₃)

δ: 8.06(br s,1 H), 7.94(d,1 H), 7.69(d,1 H), 7.39–7.48(m,1 H), 7.30–7.37(m,1 H), 7.18(d, 1 H).

The title compound (D16b) was prepared from 9-trifluoroacetylthiazolo[3,2-a]indole using the method of Description 13b and was isolated as a light purple solid (84%).

1H NMR (CDCl₃/d⁶DMSO)

δ: 7.98–8.08(m,2 H), 7.73(d,1 H), 7.10–7.31(m,2 H), 7.00(d,1 H).

Description 17

Methyl 2,4-dimethylpyrimido[1,2-a]indole-10-Carboxylate

A stirred solution of methyl 2-aminoindole-3-carboxylate (I. Forbes et al, J. Chem. Soc. Perkin 1, 1992, 275) (0.25 g, 0.0013 mole) in xylene (5 ml) was treated with 2,4-pentanedione (0.13 g, 0.0013 mole) and a few crystals of 4-toluenesulphonic acid and heated under reflux for 2 h. The mixture was concentrated in vacuo and the residue dissolved in chloroform (20 ml), washed with water (2×20 ml), dried (MgSO₄) and concentrated in vacuo to afford the title compound as a brown solid (0.25 g, 75%).

¹H NMR (CDCl₃)

δ: 8.58(d,1 H), 8.09(d,1 H), 7.52(dt,1 H), 7.34(dt,1 H), 6.53(s,1 H), 4.06(s,3 H), 3.03(s,3 H), 2.68(s,3 H).

Description 18

Methyl 1,2,3,4-tetrahydropyrimido[1,2-a]indole-10-Carboxylate

A solution of methyl 2-chloroindole-3-carboxylate (D11a, 1.5 g, 0.0071 mole) in THF (30 ml) under argon was treated with sodium hydride (215 mg of 80% oil dispersion, 0.0071 mole) and stirred for 20 minutes. The resulting solution was treated with a solution of 3-bromopropylamine (0.0093 mole) in toluene (15 ml) and a white gelatinous precipitate formed. This mixture was diluted with more THF (30 ml) and heated under reflux for 18 h, then concentrated in vacuo and the residue shaken well with ethyl acetate (40 ml) and 10% Na₂CO₃ solution (30 ml). The organic layer was separated, dried (Na₂SO₄) and concentrated in vacuo to leave a beige solid. This was chromatographed on silica gel eluting with ether/60–80 petrol (1:1) to afford unreacted starting material (600 mg) and the title compound (D 18) as a white solid (110 mg, 6%).

¹H NMR (d⁶DMSO)

δ: 7.58(d,1 H), 7.26(br s,1 H), 7.12(d,1 H), 6.88–7.05(m,2 H), 3.98(t,2 H), 3.73(s,3 H), 3.38–3.46(m,2 H), 2.08 (quintet,2 H).

Description 19

Methyl pyrimido[1,2-a]indole-10-Carboxylate

A stirred solution of methyl 2-aminoindole-3-carboxylate (I. Forbes et al, J. Chem. Soc. Perkin I, 1992, 275) (0.5 g, 0.0026 mole) in xylene (10 ml) was treated with 1,1,3,3-tetramethoxypropane (0.43 g, 0.0026 mole) and a few crystals of 4-toluenesulphonic acid and heated under reflux for 2.5 h. The mixture was concentrated in vacuo and the residue dissolved in chloroform (25 ml), washed with water (2×10 ml), dried (MgSO₄) and concentrated in vacuo to leave a dark orange solid. This was purified by chromatography on silica gel eluting with ethyl acetate to afford the title compound (D19) as an orange solid (0.23 g, 35%).

¹H NMR (CDCl₃)

δ: 8.68–8.78(m,2 H), 8.57(d,1 H), 7.89(d,1 H), 7.59(dt,1 H), 7.45(dt,1 H), 6.80–6.90(m,1 H), 4.08(s,3 H).

5-HT₄ RECEPTOR ANTAGONIST ACTIVITY

1) Guinea Pig Colon

This animal model is described by Wardle K A and Sanger G J (1993), Br J Pharmacol; 110 1593–1599.

Male guinea-pigs, weighing 250–400 g are used. Longitudinal muscle-myenteric plexus preparations, approximately 3 cm long, are obtained from the distal colon region. These are suspended under a 0.5 g load in isolated tissue baths containing Krebs solution bubbled with 5% $CO_2$ in $O_2$ and maintained at 37° C. In all experiments, the Krebs solution also contains methiothepin $10^{-7}$M and granisetron $10^{-6}$M to block effects at 5-HT₁, 5-HT₂ and 5-HT₃ receptors.

After construction of a simple concentration-response curve with 5-HT, using 30s contact times and a 15 min dosing cycle, a concentration of 5-HT is selected so as to obtain a contraction of the muscle approximately 40–70% maximum($10^{-9}$M approx). The tissue is then dosed every 15min with this concentration of 5-HT. In some experiments, this tissue was dosed alternately with an approximately equi-effective concentration of the nicotine receptor stimulant, dimethylphenylpiperazinium (DMPP). After obtaining consistent responses to 5-HT (and when appropriate, DMPP), increasing concentrations of a putative 5-HT₄ receptor antagonist are then added to the bathing solution. The effects of this compound are then determined as a percentage reduction of the contractions evoked by 5-HT or by DMPP. From this data, $pIC_{50}$ values are determined, being defined as the -log concentration of antagonist which reduces the contraction by 50%. A compound which reduces the response to 5-HT but not to DMPP is believed to act as a 5-HT₄ receptor antagonist.

Compounds were generally active as 5-HT₄ receptor antagonists in the range of concentrations of the order of $pIC_{50}$=7 or more, E1, E2, E4, E6, E8, E15 and E27 showing particularly good activity when Y is O, and E3 (SB 207266), E20, E23, E28 and E47 showing particularly good activity when Y is NH.

In the presence of 5-HT₁, 5-HT₂ and 5-HT₃ receptor antagonists, 5-HT produces a monophasic cholinergically-mediated contraction, characterised by a $pEC_{50}$ of 9.2±0.06 (n=14). Increasing concentrations of SB-207266-A, E3 as HCl salt ($10^{-10-10-8}$M, n=6) produced a parallel rightward shift of the 5-HT curve with no effect on the maximum response. The apparent $pA_2$ was 10.4±0.1, with a slope not significantly different from unity. At higher concentrations ($3 \times 10^{-8}$M and above), the maximum response to 5-HT was reduced in a concentration-dependent manner. This effect of SB-207266-A was not due to a local anaesthetic action or to a direct antagonism at cholinergic receptors, since * DMPP-evoked contractions (a nicotinic receptor agonist which evokes acetylcholine release and hence a muscarinic receptor-mediated contraction) were unaffected even by a high concentration ($10^{-5}$M) of the compound.

SB-207266-A was also tested against the contraction evoked by the 5-HT₄ receptor partial agonist BIMU 1. In these experiments, SB-207266-A reduced the maximum response to BIMU 1, without causing a prior right-ward shift in the concentration-response curve.

The apparent non-surmountable activity observed with SB-207266-A was not due to irreversible blockade of the 5-HT₄ receptor, since the antagonistic effects of SB-207266-A could be reversed upon washout. At the highest concentrations (which reduce maximum 5-HTevoked contractions), responses to 5-HT recovered within 90 minutes. Such a profile is consistent with that of a reversible antagonist.

2) Piglet Atria

Compounds are tested in the piglet atria spontaneous beating screen (Naunyn-Schmiedeberg's Arch. Pharmacol 342, 619–622).

SB-207266-A ($10^{-7}$M) shifted the curve to the right with an apparent reduction in the maximum response when compared to control curves with 5-HT alone. The estimated $pK_b$ ($-\log_{10}K_b$) of SB-207266-A (E3 as HCl salt) was 10.1 (n=2;).

3) Rat Oesophagus

Rat oesophageal tunica muscularis mucosae is set up according to Baxter et. al. Naunyn-Schmiedeberg's Arch. Pharmacol., 343, 439–446 (1991). The inner smooth muscle tube of the muscularis mucosae is isolated and mounted for isometric tension recording in oxygenated (95% $O_2$/5% $CO_2$) Tyrodes solution at 37° C. All experiments are performed in pargyline pre-treated preparations (100 $\mu$M for 15 min followed by washout) and in the presence of cocaine (30 $\mu$M). Relaxant responses to 5-HT are obtained after pre-contracting the oesophagus tissue with carbachol (3 $\mu$M). In the carbachol-contracted preparation, 5-HT produces concentration-dependent relaxations, with a $pEC_{50}$ of 8.1±0.03 (n=18). In contrast to the guinea-pig colon model, where the $5\text{-HT}_4$ receptor is neuronally-located, the receptor here is located on the smooth muscle. In the rat oesophagus preparation, SB-207266-A (E3 as HCl salt) concentration-dependently acted as a non-surmountable antagonist and reduced the maximum response evoked by 5-HT. Because SB-207266-A depressed the maximum response it was not possible to determine a reliable $pA_2$ estimate. However, the data obtained with the lowest effective concentration of SB-207266-A are consistent with a $pA_2$ of $\geq 10.0$. In view of the high selectivity of SB-207266-A as a $5\text{-HT}_4$ receptor antagonist (see previous guinea-pig isolated colon data and subsequent radioligand binding selectivity analysis), it is likely that the apparent non-surmountable antagonism is due to a slow dissociation of the compound from the receptor. This occurs because of the low $5\text{-HT}_4$ receptor reserve in rat oesophagus and the high affinity of SB-207266-A at the $5\text{-HT}_4$ receptor, relative to 5-HT itself.

4) Binding to Piglet Hippocampal $5\text{-HT}_4$ Receptors

The affinity of SB-207266-A for piglet hippocampal $5\text{-HT}_4$ receptors was determined from inhibition of binding of the $^{125}$I-labelled $5\text{-HT}_4$-antagonist SB-207710 [Brown A M, Young T J, Patch T L, Cheung C W, Kaumann A J, Gaster L M and King F D (1993), Br J Pharmacol; 110, 10P]. This radioligand has a high affinity for piglet hippocampal membranes ($K_D$=86±11 pM, $B_{max}$=16±3 fmol/mg protein (n=4)) while the $pK_i$'s for SB-207710 are 6 or less at 5-HT1A, $5\text{-HT}_1$C and $5\text{-HT}_2$ receptors. In addition, the $5\text{-HT}_3$-selective ligand granisetron inhibits [$^{125}$I]-SB-2077 10 binding in hippocampus with a pKi of below 5, indicating negligible binding of the radioligand to $5\text{-HT}_3$ receptors in this preparation. In this system, 5-HT binds to the $5\text{-HT}_4$ receptor with a moderate affinity (pKi 6.6±0.1 (n=9)). SB-207266-A inhibited the binding of $^{125}$I-labelled SB-2077 10 with a pKi value of 9.48±0.06 (n=3), a value slightly lower that the pA2/pKB estimates determined from antagonism of functional responses in other tissues.

5) Selectivity of SB-207266-A (E3 as HCl salt) in vitro

SB-207266-A has been evaluated on a variety of non-$5\text{-HT}_4$ receptor binding assays. The results are shown in the Table below. Functional studies on the rat stomach fundus reveal an affinity for the $5\text{-HT}_{2B}$ receptor of 7.47. Clearly there are several orders of magnitude of selectivity for the $5\text{-HT}_4$ receptor over the other receptors tested.

| Receptor Binding Studies | $pK_d$ |
|---|---|
| $5\text{-HT}_{1A}$ | <5.00 |
| $5\text{-HT}_{1D}$ | <5.00 |
| $5\text{-HT}_{1E}$ | <5.00 |
| $5\text{-HT}_{2A}$ | 5.89 |
| $5\text{-HT}_{2C}$ | 5.57 |
| $5\text{-HT}_3$ | 5.94 |
| Alpha$_1$ | <5.52 |
| $D_2$ | 5.63 |
| $D_3$ | 5.53 |
| GABA | >5.00 |
| BDZ | >5.00 |
| $H_1$ | 5.40 |
| Opiate kappa | (pKi) >6 |
| Opiate mu | (pKi) >6 |
| Opiate delta | (pKi) >6 |

4) 5-HT-Induced Motility in Dog Gastric Pouch

Compounds are tested for inhibition in the in vivo method described in "Stimulation of canine motility by BRL 24924, a new gastric prokinetic agent", Bermudez et al, J. Gastrointestinal Motility, 1990, 2(4), 281–286.

Dogs with previously prepared Heidenhain gastric pouches are fasted overnight. For each dog, dose-ranging studies with 5-HT are also performed previously to ascertain the minimal intravenous (iv) dose which evokes a reproducible, cholinergically-mediated increase in tonic and phasic gastric contractility, usually 5 or 10 ug.kg$^{-1}$. For each experiment, 5-HT is administered iv at 30 min intervals. After two consistent responses, antagonists are injected iv or dosed po in a gelatine capsule 15 min before the third injection of 5-HT.

Both iv and po, SB-207266-A dose-dependently antagonised the contractile response to 5-HT [$ID_{50}$ 1.3 (Confidence Limits 0.1–14.0) ug.kg$^{-1}$ iv, 9.6 (CL 0.7–128) ug.kg$^{-1}$ po]. Furthermore there was no effect of SB-207266-A at any dose on basal motility. There was no consistent or significant effect with $5\text{-HT}_1$, $5\text{-HT}_2$ and $5\text{-HT}_3$ receptor antagonists.

The duration of action of SB-207266-A was determined after iv dosing. At the lower doses of 1 and 3 ug.kg$^{-1}$ the effects were variable and apparently reversible, whilst at 10 and 100 ug.kg$^{-1}$, the antagonism lasted for more than the duration of the experiment (285 minutes).

5) Antagonism in Anaesthetised Piglets

In these experiments, antagonism is assessed against the 5-HT-evoked tachycardia, a response that is mediated by the $5\text{-HT}_4$ receptors. All experiments were in 2–5 day old piglets in which the vagi were sectioned. SB-207266-A (E3 as HCl salt) at doses of 0.1, 0.3 or 1.0 ugkg$^{-1}$ given intravenously antagonised the 5-HT-evoked tachycardia in a dose-dependent manner (n=2 each). At doses which substantially antagonise this $5\text{-HT}_4$ receptor mediated effect of 5-HT (0.3, 1.0 ugkg$^{-1}$ i.v.), the recovery from antagonism was incomplete, over the duration of the experiment.

PREVENTION OF 5-HT-INDUCED DIARRHOEA

1) Distension-Evoked Peristalsis in Guinea Pig Isolated Ileum

The potential of SB-207266-A (E3 as HCl salt) to antagonise the increased sensitivity of the peristaltic reflex evoked by 5-HT in guinea-pig isolated ileum has been evaluated.

The response to 5-HT has been shown to be mediated via the $5\text{-HT}_4$ receptor [Craig D A and Clarke D E (1991), Br J Pharmacol; 102, 563–564]. Sections of guinea-pig ileum were fixed in a horizontal organ bath filled with Krebs solution containing $5\text{-HT}_1$, $5\text{-HT}_2$ and $5\text{-HT}_3$ receptor antagonists. The oral end was connected to a Krebs-filled reservoir and the aboral end to a vertical column open to the air. The intraluminal filling pressure (oral end) and peristaltic pressure (aboral end) were monitored. The threshold pressure for peristalsis was determined by raising the reservoir at increments of 0.5 cm $H_2O$ at 1 min intervals until peristalsis occurred. Distending the ileum to a sub-threshold level then adding 5-HT ($10^{-7}$M) to the serosal side, induced peristalsis. At $10^{-11}$M, SB-207266-A had no ability to antagonise this sensitising effect of 5-HT in 4/4 tissues. At $10^{-10}$M, SB-207266-A antagonised the action of 5-HT in 3/4 tissues. At $10^{-9}$M, the sensitising effect of 5-HT was abolished in 3/3 preparations.

2) Antagonism in Conscious Fed Mice

A model was developed to examine the effect of $5-HT_4$ receptor antagonists on large bowel motility (faecal pellet output, FPO) and fluid secretion (pellet wet/dry weight) during 'fed' conditions. The antagonists are studied in normal mice (to determine adverse effects, eg constipation) and in mice with functional diarrhoea caused by 5-HTP [Banner S E, Smith M I, Bywater D and Sanger G J (1993), Br J Pharmacol, 110, 17 P, and Banner S E, Smith M I and Sanger G J (1993) Br J Pharmacol; 110, 135 P]. Faecal pellets were collected at 10 min intervals so that their number and wet/dry weights could be determined.

SB-207266-A (E3 as HCl salt) was administered s.c. or po to mice pre-dosed with either saline or 5-HTP (10 mg kg$^{-1}$ s.c). This dose of 5-HTP increased FPO above control levels; higher doses evoked watery diarrhoea and unformed faecal output. The maximum effect of 5-HTP at 10 mgkg$^{-1}$ s.c was seen after 20 min and the analysis of 5-HT receptor antagonist activity was carried out at this time point. SB-207266-A did not affect either FPO or their fluid content in normal mice, which were not pretreated with 5-HTP. However, SB-207266-A administered s.c. dose-dependently prevented the 5-HTP-evoked increase in FPO (0.1 to 10 ug.kg$^{-1}$); fluid secretion evoked by 5-HTP was also prevented by SB-207266-A. Further experiments show that SB-207266-A can also reduce the watery diarrhoea caused by a high (50 mg.kg$^{-1}$) dose of 5-HTP. The $5-HT_1$, $5-HT_2$ and $5-HT_3$ receptor antagonists either had no effect or at best tended to reduce, but not prevent the 5-HTP induced increase in FPO.

Orally-administered SB-207266-A (10–1000 ug.kg$^{-1}$) greatly reduced the effects of 5-HTP when given 30 min prior to 5-HTP. Predosing the mice with SB-207266-A 100 ug.kg$^{-1}$ enabled an estimation of duration of action to be made. At this dose, the compound was without effect when pre-dosed 6 hours before 5-HTP, but was effective when dosed 2.5 hours before 5-HTP.

IN VIVO TESTING FOR ANXIOLYTIC ACTIVITY

Social Interaction Test in Rats

Rats (male, Sprague Dawleys, Charles River, 250–300 g) are housed in groups of eight in a holding room for 5 days. They are then housed singly in a room adjacent to the experimental room for 4 days prior to the experimental day. On the experimental day rats are administered vehicle, test compound or a benzodiazepine anxiolytic, chlordiazepoxide, p.o. in pairs (n=8–16), at 15 minute intervals beginning at 10.00 a.m. 30 mins. later they are placed with a weight matched pair-mate (encountered for the first time) in the social interaction box in a separate room. The box is made of white perspex 54 cm×37 cm×26 cm with a transparent perspex front side and no lid. The floor is divided up into 24 squares and the box is brightly lit (115 lux). Active social interactive behaviours (grooming, sniffing, climbing over or under, following, biting, mounting and boxing) are scored blind for the next 15 min by remote video monitoring to give total interaction scores. The number of squares crossed by each rat is also scored and summed. After the end of each test the box is carefully wiped.

Significantly increased total interaction scores were observed 1 h after administration of SB-207266-A, E3 as HCl salt (0.01, 1, 10 mg.kg$^{-1}$). The magnitude of this effect was somewhat smaller than that of the positive control chlordiazepoxide (CDP; 5 mg.kg$^{-1}$ po) but not significantly so. The effect of SB-207266-A was not accompanied by any alteration in locomotion during the test and hence is consistent with anxiolysis.

What we claim is:

1. N-[(1-"Butyl-4-piperidyl)methyl]-3,4-dihydro-2 H-[1,3]oxazino[3,2-a]indole-10-carboxamide or a pharmaceutically acceptable salt thereof.

2. N-[(1-"Butyl-4-piperidyl)methyl]-3,4-dihydro-2 H-[1,3]oxazino[3,2-a]indole- 10-carboxamide hydrochloride.

3. A pharmaceutical composition comprising a compound according to claim 1, and a pharmaceutically acceptable carrier.

4. A method of treating irritable bowel syndrome comprising administering a compound according to claim 1.

5. A method of treating urinary incontinence comprising administering a compound according to claim 1.

6. A method of treating atrial arrhythmia or stroke comprising administering a compound according to claim 1.

* * * * *